(12) United States Patent
Chen et al.

(10) Patent No.: US 6,235,729 B1
(45) Date of Patent: May 22, 2001

(54) USES OF PHOSPHOLIPASE C INHIBITORS

(75) Inventors: Philip Chen, Birmingham; Timothy Turner, Auburn; Alan Wells, Birmingham, all of AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 08/824,149

(22) Filed: Mar. 25, 1997

Related U.S. Application Data

(60) Provisional application No. 60/014,308, filed on Mar. 27, 1996, now abandoned.

(51) Int. Cl.⁷ .......................... A61K 31/58; A61K 31/27
(52) U.S. Cl. ............................................. 514/176; 514/477
(58) Field of Search ...................................... 514/176, 477

(56) References Cited

PUBLICATIONS

Turner et al., Clin. Exp. Mrtastasis, 14(4), 409–418 Abstract Only, 1996.*
Berger et al, Oncology, 41(2), 109–13 Abstract Only, 1984.*
Scherf et al., Lipids 22(11), 927–9 Abstract Only, 1987.*
Bruyneel et al., Pharmacol. Eff. Lipids, 3, 301–8 Abstract Only, 1989.*
Pai et al., Anti–Cancer Drug Des., 9(4), 363–72 Abstract Only, 1994.*

* cited by examiner

*Primary Examiner*—Jerome D. Goldberg
(74) *Attorney, Agent, or Firm*—Benjamin Aaron Adler

(57) ABSTRACT

The present invention provides a method of inhibiting tumor progression in an individual in need of such treatment, comprising the step of administering to said individual a pharmacologically effective dose of a phospholipase C inhibitor. Also provided is a method of inhibiting metastasis in an individual in need of such treatment, comprising the step of administering to said individual a pharmacologically effective dose of a phospholipase C inhibitor. Further provided are pharmaceutical compositions, comprising a phospholipase C inhibitor of tumor invasiveness and metastasis and a pharmaceutically acceptable carrier and a pharmaceutical composition, comprising a phospholipase C inhibitor of tumor invasiveness and metastasis, a antineoplastic agent and a pharmaceutically acceptable carrier.

4 Claims, 22 Drawing Sheets

(3 of 22 Drawing Sheet(s) Filed in Color)

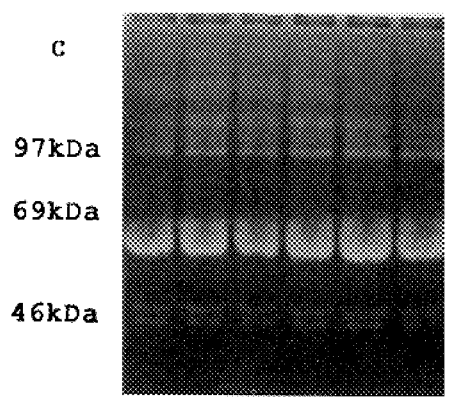
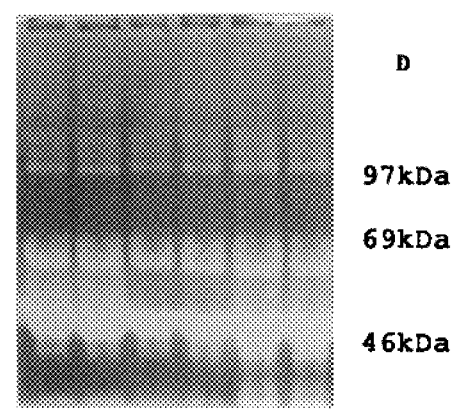
FIGURE 5C
FIGURE 5D

Control

U73122

USES OF PHOSPHOLIPASE C INHIBITORS

CROSS-REFERENCE TO RELATED APPLICATION

This application claims benefit of provisional application Ser. No. 60/014,308 filed Mar. 27, 1996, now abandoned.

BACKGROUND OF THE INVENTION

1. Field of the Invention

The present invention relates generally to the fields of tumor and cell biology, pharmacology and protein chemistry. More specifically, the present invention relates to a novel uses of phospholipase C inhibitors.

2. Description of the Related Art

Prostate tumor invasion and metastatic spread present major obstacles to successful cancer control. The critical step in tumor progression is the ability to transmigrate an extracellular matrix and reach the general circulation or invade adjacent tissues. Transmigration of an extracellular matrix (ECM) is a complex process which requires active interactions between the invading cell and the extracellular matrix and other stromal elements [1, 2]. At least three processes are necessary for cell invasiveness: tumor cell recognition of and adhesion to the extracellular matrix, proteolytic remodeling or destruction of the extracellular matrix, and cell migration through the resultant defect. The relative contributions of these processes to cell invasiveness may vary under different circumstances.

The receptor for the epidermal growth factor (EGF) is the peptide growth factor receptor most often found upregulated in human carcinomas [13]. Epidermal growth factor receptor (EGFR) gene amplification or elevated levels of epidermal growth factor binding sites correlate with tumor progression to invasiveness and metastasis. Gene amplification is noted in the majority of glioblastomas but is not seen in encapsulated gliomas [14, 15]. Increased levels of epidermal growth factor receptor are detected in invasive bladder carcinoma [16, 17] and advanced gastric carcinoma [18]; and elevated levels of epidermal growth factor receptor correlate with metastasis and decreased survival in breast cancer patients [19, 20]. In an experimental model system, metastatic potential of human colon carcinoma cells correlated with epidermal growth factor receptor level and functioning [21]. This finding is similar to metastasis of a non-small cell lung carcinoma line being dependent on the level of the epidermal growth factor receptor-related c-erbB-2/neu [22]. In vitro exogenous epidermal growth factor has been shown to promote thyroid tumor cell invasiveness through matrigel [23].

Prostate carcinoma is the most widespread malignancy encountered in the human male population. The frequency and mortality rate of prostate cancer has increased over the past 40 years and is expected to rise steadily in the impending years (1). Androgen dependency of prostate carcinoma usually accompanies initial neoplastic growth, during which tumors respond favorably to hormonal therapy. However, androgen-independent tumors often emerge (2). Deaths related to prostate cancer are invariably due to tumor invasion and metastasis to the lungs, skeleton, and lymph nodes (1, 3). Once the tumor escapes it natural surroundings to invade and metastasize, none of the available treatments yield positive affects on patient survival (3–6). Consequently, efforts to improve the understanding of the basic biology of this disease and particularly the progression to the invasive and metastatic stages should enhance the chances for developing therapeutic approaches.

Polypeptide hormones or growth factors play important roles in the normal and pathologic development of the prostate. Various growth factors promote cell proliferation, motility, and invasiveness of epithelial cells in vitro, all properties required for tumor invasiveness and metastasis. Growth of explanted cells is stimulated by nonsteroidal growth factors, such as epidermal growth factor, (7) and not by steroids such as DHT (8, 9). Prostatic fluid has the highest concentration of epidermal growth factor in the human body (10). Numerous epidermal growth factor-like factors are expressed by normal and neoplastic prostatic cells (9, 11–14). Recent evidence suggests androgens stimulate prostate proliferation in the androgen-dependent cell line, ALVA-31, by upregulating an autocrine stimulatory growth loop involving the epidermal growth factor receptor and one of its ligands, transforming growth factor-α (TGF-α) (14). However, the roles of epidermal growth factor receptor and its ligands in tumor progression have not been defined.

Epidermal growth factor receptor, a transmembrane protein which possesses intrinsic tyrosine kinases activity, is the growth factor receptor found most often upregulated in human carcinomas (15). In an animal model, a direct correlation was seen in the metastatic potential of human colon carcinoma cells and epidermal growth factor receptor level and function (23). Examination of normal prostate epithelial, benign prostatic hyperplasia (BPH) and carcinoma cells demonstrate increased levels of epidermal growth factor receptor expression as one progresses through the different hyperproliferative states (9, 24), the highest levels of epidermal growth factor receptor expression correlating with the loss of androgen-dependency by prostate carcinoma cells (25). In prostate cancer, one detects either an increase in the level of epidermal growth factor receptor (25, 26) or in the production of its activating ligands, epidermal growth factor and transforming growth factor-α (9, 27), or both (28, 29). In many cancers, the synchronous overexpression of epidermal growth factor/transforming growth factor-α and epidermal growth factor receptor has been associated with more invasive phenotypes (30–33). This autocrine stimulatory loop is often present in prostate carcinoma, e.g., in the DU-145 human prostate carcinoma cell line (34), which produces transforming growth factor-α and expresses epidermal growth factor receptor (28, 29, 35, 36).

Previously, DU-145 cells were genetically-engineered to overexpress a full length, wild-type epidermal growth factor receptor in order to delineate the role epidermal growth factor receptor signaling plays in cell proliferation and invasion (36). In vitro transmigration of a human extracellular matrix was increased for the cells overexpressing wild type epidermal growth factor receptor. Disruption of the transforming growth factor-α-epidermal growth factor receptor autocrine stimulatory loop by an epidermal growth factor receptor antibody diminished DU-145 parental and wild type epidermal growth factor receptor-expressing cell invasion through the extracellular matrix in vitro; thus emphasizing the importance of epidermal growth factor receptor signaling in cell migration and invasion. Epidermal growth factor receptor-dependent migration and invasion observed in DU-145 sublines expressing wild type epidermal growth factor receptor was not linked to increased proteolytic activity (36), but did correlate with signals which lead to increased cell motility (37, 38).

The prior art is deficient in the lack of effective means of inhibiting tumor cell motility which is critical for tumor invasion and metastasis. The present invention fulfills this longstanding need and desire in the art.

SUMMARY OF THE INVENTION

Prostate carcinomas often present an autocrine stimulatory loop in which the transformed cells both express the epidermal growth factor receptor and produce activating ligands (transforming growth factor-α and epidermal growth factor forms). Upregulated epidermal growth factor receptor signaling has been correlated with tumor progression in other human neoplasias; however, the cell behavior which is promoted remains undefined. To determine whether an epidermal growth factor receptor-induced response contributes to cell invasiveness, DU-145 human prostate carcinoma cells were transduced with either a full-length (wild type) or a mitogenic-active but motility-deficient, truncated (c'973) epidermal growth factor receptor. The DU-145 parental and two transgene sublines all produced epidermal growth factor receptor and transforming growth factor-α, but the transduced wild type and c'973 epidermal growth factor receptor underwent autocrine downregulation to a lesser degree, with more receptor mass remaining intact.

DU-145 cells transduced with wild type epidermal growth factor receptor transmigrated a human amniotic basement membrane matrix (Amgel) to a greater extent than did Parental DU-145 cells (175±22%). Cells expressing the c'973 epidermal growth factor receptor invaded through the Amgel only to about 65% the extent of Parental cells (62±23%). A monoclonal antibody which prevents ligand-induced activation of epidermal growth factor receptor decreased the invasiveness of wild type-expressing cells by half and Parental cells by a fifth, but had little effect on the invasiveness of c'973-expressing cells; with the result that in the presence of the antibody, all three lines transmigrated the Amgel matrix to a similar extent. The different levels of invasiveness between the three sublines were independent of cell proliferation. These findings demonstrated that epidermal growth factor receptor-mediated signals increase tumor cell invasiveness and suggested that domains in the carboxy-terminus are required to signal invasiveness. As an initial investigation into the mechanisms underlying the epidermal growth factor receptor-mediated enhanced invasiveness, it was determined whether these cells presented differential collagenolytic activity, as the major constituents of Amgel are collagen types I and IV. All three sublines secreted easily detectable levels of gelatin-directed proteases and TIMP-1, with wild type cells secreting equivalent or lower levels of proteases. The proteolytic balance in these cells did not correlate with the invasiveness. These data suggest that the transforming growth factor-α-epidermal growth factor receptor autocrine loop promotes invasiveness by signaling cell properties other than differential secretion of collagenolytic activity.

To determine whether up-regulated epidermal growth factor receptor signaling promotes tumor progression in vivo and to define the epidermal growth factor receptor-induced cell property responsible, athymic mice were inoculated with genetically-engineered DU-145 cells. Parental DU-145 cells and those transduced to overexpress a full-length (wild type) epidermal growth factor receptor formed tumors and metastasized to the lung when inoculated in the prostate and peritoneal cavity. The wild type DU-145 tumors were more invasive. DU-145 cells expressing a mitogenically-active, but motility-deficient (c'973) epidermal growth factor receptor formed small, non-invasive tumors without evidence of metastasis. All three sublines demonstrated identical, epidermal growth factor receptor-dependent rates of cell growth in vitro, suggesting that the differential invasiveness was not due to altered growth rates. To determine whether cell motility may be, in part, responsible for tumor invasiveness, wild type DU-145 intraperitoneal tumors were treated with a pharmacologic inhibitor of phospholipase C (U73122). Under this treatment regimen, the wild type DU-145 cells formed tumors of similar numbers and size to those formed without treatment; however, these tumors were much less invasive. These data suggest that epidermal growth factor receptor-mediated cell motility is an important mechanism involved in tumor progression, and that this cell property represents a novel target to limit the spread of tumors. Further shown was whether epidermal growth factor receptor-mediated signaling promotes tumor progression in vivo. Three DU-145 sublines were inoculated either into the prostate (to reflect an in situ lesion) or peritoneal cavity (to recapitulate the initial stages of localized invasiveness) of athymic mice. Tumor formation and invasiveness was assessed histologically. The mechanism by which epidermal growth factor receptor signaling promotes tumor progression was probed by treatment with a pharmacologic agent which prevents epidermal growth factor receptor-mediated cell motility by inhibiting phospholicpase C.

In one embodiment of the present invention, there is provided a method of inhibiting tumor progression in an individual in need of such treatment, comprising the step of administering to said individual a pharmacologically effective dose of a phospholipase C inhibitor.

In another embodiment of the present invention, there is provided a method of inhibiting tumor metastasis in an individual in need of such treatment, comprising the step of administering to said individual a pharmacologically effective dose of a phospholipase C inhibitor.

In yet another embodiment of the present invention, there is provided a pharmaceutical composition, comprising a phospholipase C inhibitor of tumor invasiveness and metastasis and a pharmaceutically acceptable carrier.

In still yet another embodiment of the present invention, there is provided a pharmaceutical composition, comprising a phospholipase C inhibitor of tumor invasiveness and tumor metastasis, a antineoplastic agent and a pharmaceutically acceptable carrier.

Other and further aspects, features, and advantages of the present invention will be apparent from the following description of the presently preferred embodiments of the invention given for the purpose of disclosure.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 9 shows the inhibition of DU-145 cell growth by interruption of epidermal growth factor receptor-transforming growth factor-a autocrine pathway by an anti-epidermal growth factor receptor antibody.

FIG. 10 demonstrates that cell proliferation and viability are not adversely affected by U73122.

DETAILED DESCRIPTION OF THE INVENTION

Figure 1A:
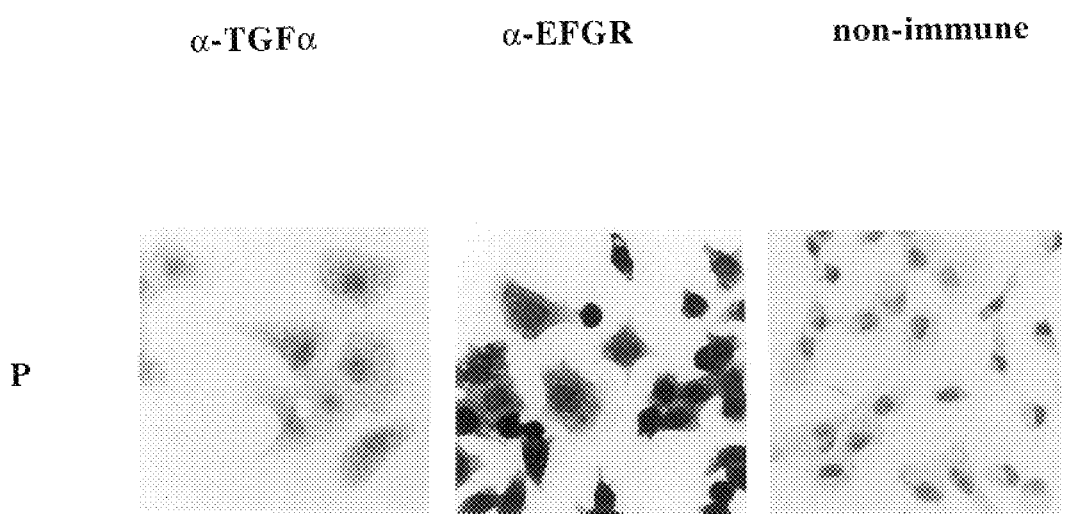
FIG. 1 shows the production of transforming growth factor-α and expression of epidermal growth factor receptor on Parental (P) (FIG. 1A) and infectant DU-145 sublines wild type (FIG. 1B) and c'973 (FIG. 1C). Cells were analyzed by immunohistochemistry as described below. Transforming growth factor-α protein was found in a cytoplasmic distribution, predominantly perinuclear as expected for a rough endoplasmic reticulum pattern of secreted proteins. Epidermal growth factor receptor was detected in a pattern consistent with surface expression.

The present invention is directed to a method of inhibiting tumor progression in an individual in need of such treatment, comprising the step of administering to said individual a pharmacologically effective dose of a phospholipase C inhibitor. Preferably, the phospholipase C inhibitor is selected from the group consisting of U73122 (1-(6-((17β-3-methoxyestra-1,3,5(10)-trien-17-yl)amino)hexyl)-1H-pyrrole-2,5-dione), ET-18-OCH$_3$ (1-O-octadecyl-2-O-methyl-sn-glycero-3-phosphorylcholine), and RHC-80267 (1,6-bis-(cyclohexyloximinocarbonylamino)-hexane). A person having ordinary skill in this art, given the teachings of the present specification as disclosed below, would readily be able to prepare other phospholipase C inhibitors useful in slowing or inhibiting tumor invasiveness and metastasis. Preferably, the phospholipase C inhibitor decreases phospholipase Cγ. Generally, such a phospholipase C inhibitor would be administered in a dose of from about 0.1 mg/kg to about 2 mg/kg. As used herein, the term "inhibiting tumor progression" should be taken to mean demonstrably reducing tumor cell invasion through an encapsulating extracellular matrix, invasion into an organ (e.g., bladder or kidney) or structure (e.g., ureter or diaphragm), or metastases to lymph nodes or distant sites. Evidence for such an effect can be obtained by many standard diagnostic methods including imaging and histologic analyses.

The present invention is also directed to a method of inhibiting tumormetastasis in an individual in need of such treatment, comprising the step of administering to said individual a pharmacologically effective dose of a phospholipase C inhibitor. Preferably, the phospholipase C inhibitor decreases phospholipase Cγ. Preferably, the phospholipase C inhibitor is selected from the group consisting of U73122, ET-18-OCH$_3$, and RHC-80267. Generally, such a phospholipase C inhibitor would be administered in a dose of from about 0.1 mg/kg to about 2 mg/kg. As used herein, the term "inhibiting metastasis" should be taken to mean demonstrably reducing the number and/or size of tumor growths in a site distal from the site of origin. For prostate cancer, metastatic spread appears preferentially but not exclusively in lymph nodes, bone marrow, lungs and liver. Evidence for such a reduction can be obtained by many standard diagnostic methods including imaging and histologic analyses.

It is specifically contemplated that pharmaceutical compositions may be prepared for the phospholipase C inhibitors for use in the novel methods of the present invention. In such a case, the pharmaceutical composition comprises the phospholipase C inhibitor of the present invention and a pharmaceutically acceptable carrier. Preferably, the phospholipase C inhibitor decreases phospholipase Cγ. A person having ordinary skill in this art would readily be able to determine, without undue experimentation, the appropriate dosages and routes of administration of the phospholipase C inhibitor of the present invention.

The present invention is also directed to novel pharmaceutical composition, comprising a phospholipase C inhibitor of tumor invasiveness and tumor metastasis and a pharmaceutically acceptable carrier. In one embodiment, the phospholipase C inhibitor is U73122.

The present invention is also directed to pharmaceutical compositions, comprising a phospholipase C inhibitor of tumor invasiveness and metastasis, a antineoplastic agent and a pharmaceutically acceptable carrier.

Administration of the compositions of the present invention may be by topical, intraocular, parenteral, oral, intranasal, intravenous, intramuscular, subcutaneous, intraperitoneal, direct intraneoplasia injection, or any other suitable means. The dosage administered is dependent upon the age, clinical stage and extent of the disease or genetic predisposition of the individual, location, weight, kind of concurrent treatment, if any, and nature of the pathological or malignant condition. The effective delivery system useful in the method of the present invention may be employed in such forms as capsules, tablets, liquid solutions, suspensions, or elixirs, for oral administration, or sterile liquid forms such as solutions, suspensions or emulsions. Any inert carrier is preferably used, such as saline, or phosphate-buffered saline, or any such carrier in which the novel compounds used in the method of the present invention have suitable solubility properties.

Preferably, delivery systems useful in the method of the present invention may be employed in such sterile liquid forms such as solutions, suspensions or emulsions; delivered by means such as intermittant injections or continuous pumps. For topical use it may be employed in such forms as ointments, creams or sprays. Any inert carrier is preferably used, such as saline, or phosphate-buffered saline, or any such carrier in which the compounds used in the method of the present invention have suitable solubility properties.

There are a wide variety of pathological cancerous and noncancerous cell proliferative conditions for which the compositions and methods of the present invention will provide therapeutic benefits. Among the cell types which exhibit pathological or abnormal growth are (1) fibroblasts, (2) vascular endothelial cells, (3) epithelial cells and (4) glial or other mesenchyme-derived cell. It can be seen from the above that the methods of the present invention are useful in treating local or disseminated pathological conditions in all or almost all organ and tissue systems of the individual.

The following examples are given for the purpose of illustrating various embodiments of the invention and are not meant to limit the present invention in any fashion.

EXAMPLE 1

Retrovirus Vectors Containing Epidermal Growth Factor Receptor

The construction of the epidermal growth factor receptor was by standard methods [39]. Wild type epidermal growth factor receptor is a full-length cDNA [40] derived from a placental cDNA library [41]. When expressed in appropriate cells, this construct elicits all the responses of wild type epidermal growth factor receptor. c'973 epidermal growth factor receptor represents a carboxy-terminal truncated epidermal growth factor receptor in which a stop codon was introduced just distal to amino acid 973. This construct presents ligand-induced kinase and mitogenic activities but does not possess phosphotyrosine motifs or induce cell motility. The epidermal growth factor receptor constructs were cloned into a murine moloney leukemia virus-based retroviral expression vector in the gag position. An SV40 early promoter and neomycin phosphotransferase gene, as the selectable marker, were cloned in the env position. Purified plasmid was transfected into PA-137 amphotropic producer cells using the lipofectin reagent (Gibco/BRL) [36]. Polyclonal producer lines were established from >20 G418-resistant (350 µg/ml) colonies.

EXAMPLE 2
Cell Culture and Infection

DU-145 cells, originally derived from a human prostate carcinoma brain metastasis [30], were grown in Dulbecco's modified Eagle's medium/F12 (50/50) media supplemented with fetal bovine serum (FBS) (7.5%), penicillin (100 U/ml), streptomycin (200 µg/ml), non-essential amino acids, sodium pyruvate (1 mM), and glutamine (2 mM) (37° C., 90% humidity, 5% $CO_2$). Cells were passaged at subconfluence by trypsinization (0.25%, 1 mM EDTA).

Infection of cells by retroviruses containing epidermal growth factor receptor constructs was accomplished by established protocols [39]. Briefly, cells were seeded at ~30% confluence. After cells were allowed to attach overnight, the media was replaced with cell-free, virus-containing PA-137 conditioned media containing polybrene (4 µg/ml). Three hours later, an equal volume of growth media was added and the incubation continued for an additional three hours. The cells were then washed and incubated in growth media for 48 hours prior to selection in G418 (Gibco/BRL) (1000 mg/ml). Polyclonal lines consisting of >20 colonies were established and maintained in G418-containing media. DU-145 cells transduced with either the WT epidermal growth factor receptor or c'973 epidermal growth factor receptor construct hereafter are referred to as wild type cells or c'973 cells, respectively. Un-infected DU-145 cells are referred to as Parental cells.

EXAMPLE 3
Epidermal Growth Factor Receptor Detection Assays

Presence of epidermal growth factor receptor on the surface of infectant cells was determined by epidermal growth factor binding and immunodetection of epidermal growth factor receptor (below). Scatchard analyses determined the apparent binding site number and affinity for epidermal growth factor. Cells were seeded in 12-well culture plates (~300,000 cells/well). The cells were stripped of prebound, autocrine ligand by incubation at pH 2.5 for 10 minutes [42]. After two washes with PBS, the cells were incubated for 30 minutes in serum-free media, followed by incubation (4° C. for 2 hours) in binding buffer (DME with 25 mM HEPES, pH7.4, and 0.2% BSA) containing 0.1 nM $^{125}I$ labeled-epidermal growth factor and unlabeled epidermal growth factor (0 to 100 nM). Unbound $^{125}I$-epidermal growth factor was collected from the supernatant and two subsequent washes with binding buffer. The cells were lysed to liberate the bound $^{125}I$-epidermal growth factor, which was collected. Free and bound $^{125}I$-epidermal growth factor were counted and the $B_{max}$ and $K_d$ values for each cell line were calculated from scatchard plots after subtracting background counts (radioactivity bound in the presence of 10–100 nM epidermal growth factor).

EXAMPLE 4
Immunohistochemical Detection of Epidermal Growth Factor Receptor and Transforming Growth Factor-α

Cells were trypsinized and plated onto glass coverslips. The cells were grown for 2–3 days to all surface proteins to be resynthesized. Cells were washed twice in PBS, fixed in 10% buffered formalin, processed, and stained by standard procedures. Briefly, tissues were passed through a series of ethanol and acetone washes for dehydration and fixation. To prevent nonspecific staining, hydrogen peroxide (3%) incubation for 5 minutes quenched endogenous peroxidase activity. For detection of epidermal growth factor receptor, cells were pretreated with 0.05% saponin for 30 minutes, washed, blocked with 1% non-immune rabbit serum for 60 minutes (room temperature), and incubated with a monoclonal epidermal growth factor receptor antibody (5 µg/ml) (AB-1, Oncogene Science) for 60 minutes. For detection of transforming growth factor-α, cells were blocked with normal rabbit serum and then probed with a monoclonal transforming growth factor-α antibody (10 µg/ml) (courtesy of J Kudlow, UAB [27]) overnight (4° C.). Unbound antibody was removed by several washes in PBS, and antigen was visualized using the biotin-streptavidin detection HRP super-sensitive system (Biogenex). Cells were counterstained with hematoxylin to visualize all nuclei.

EXAMPLE 5
In Vitro Invasion Assay

Amgel, a human extracellular matrix, was prepared from normal full-term human placenta amniotic membranes as previously described [38]. The major constituents of Amgel are collagen types I and IV, laminin, entactin, tenascin, and heparan sulfate proteoglycan. epidermal growth factor and transforming growth factor-α are not detected in this matrix, in contrast to EHS-derived Matrigel [38, 43, 44]. Furthermore, by employing a human-derived extracellular matrix, species homogeneity for all parameters of the assay-cells, extracellular matrix, and epidermal growth factor receptor was maintained.

Cell invasiveness was measured in a modified chamber assay. 100 mg Amgel was layered onto a polycarbonate filter (8 mm pore; 8 mm diameter). Uniformity of coating was ascertained by coomassie blue staining of a parallel well. Cells were labeled metabolically with $^3H$-thymidine (1 mCi/ml) for 20 hours. Cells were washed of unincorporated thymidine and seeded onto the Amgel-coated filters (50,000 cells/well in 0.4 ml Dulbecco's modified Eagle's medium/ 0.2% bovine serum albumin). The lower chamber contained Dulbecco's modified Eagle's medium supplemented with 10% FBS. The chambers were incubated at 37° C. (90% humidity, 5% $CO_2$) for 24 hours, after which the media in the upper chamber was replaced with Dulbecco's modified Eagle's medium (without bovine serum albumin). After a further 48 hour incubation cells were harvested from the lower chamber and the underside of the filter. Quantitation of cells was performed by scintillation counting and percent transmigration calculated. All experiments were performed in quadruplicate. In all experiments a highly invasive fibrosarcoma cell line, HT1080, served as the positive control. Determining the percentage of label, rather than number of cells, that was present in the lower chamber avoided potential over-estimation of transmigration which may occur secondary to cell proliferation.

In the antibody inhibition studies, cells were mixed with antibodies just prior to seeding onto the Amgel-coated filters. A non-activating, anti-epidermal growth factor receptor monoclonal antibody (4 µg/ml) which prevents epidermal growth factor binding (528) [45] was utilized to prevent epidermal growth factor receptor-mediated signaling. Non-specific murine IgG served as a control in these assays.

EXAMPLE 6
Collection of Secreted Proteins

Cells were plated at 60–80% confluence directly onto plastic culture dishes or dishes coated with Amgel. Cells were allowed to attach in media containing 7.5% FBS, and 12 to 14 hours later were switched to media containing 1% dialyzed PBS (dFBS). This level of dFBS was required to maintain cell viability while quiescing the cells [36]. Cells plated on plastic were treated with or without epidermal growth factor (10 nM). A saturating level of epidermal growth factor was maintained for the entire assay period [46]. Conditioned media was collected over one of two 14 hour periods, either 0–14 or 34–48 hours. The conditioned media was clarified by centrifugation at 1000×g for 5 minutes. Protein was precipitated from the supernatant using 60% ammonium sulfate. The protein pellet was dissolved in 50 mM Tris (pH 7.4), and dialyzed against TBS (25 mM Tris (pH 7.4), 150 mM NaCl). Protein quantitation was performed using the Bradford method (Pierce).

EXAMPLE 7
Immunoblotting Detection of Proteins

Proteins were separated by SDS-PAGE (polyacrylamide gel electrophoresis), using standard procedures. Samples were boiled in SDS-PAGE buffer under reducing conditions (5% β-mercaptoethanol). After electrophoretic separation, the proteins were transfered to a PVDF membrane (Millipore). Epidermal growth factor receptor was detected using a monoclonal antibody directed against an extracellular epitope (LA22, Oncogene Sciences). Tissue inhibitors of metalloproteases-1 using rabbit polyclonal antisera were obtained from Dr. K. Bodden, UAB). Tissue inhibitors of metalloproteases-2 using a monoclonal antibody were obtained from K. Bodden; MMP-9 (92 kDa gelatinase) using rabbit polyclonal antisera and MMP-2 (72 kDa gelatinase) using a monoclonal antibody were obtained from K. Bodden. Visualization was accomplished with a second antibody conjugated to alkaline phosphatase followed by color development (ProtoBlot system; Promega).

EXAMPLE 8
Zymography for Proteolytic Activity

Collagenolytic and plasminogen-dependent collagenolytic activities were detected by the SDS-PAGE-zymography method [47, 48]. 7.5% polyacrylamide gels were copolymerized with 0.15% gelatin; a subset of these gels also included plasminogen (1 µg/ml). Protein samples were mixed with PAGE sample buffer (without reducing agents, and without heating/boiling) before loading on the 4% stacking gel. SDS was removed from the gels by washing twice for 30 minutes in 50 mM Tris (pH7.4) containing 2.5% Triton X-100 and then twice for 5 minutes in 50 mM Tris (pH 7.4). The gels were incubated either 3 hours at 37° C. or overnight at 22° C. in digestion buffer (50 mM Tris (pH7.4), 200 mM NaCl, 10 mM $CaCl_2$, 1% Triton X-100). Lysis zones were visualized after staining with amido black.

EXAMPLE 9
RNA Isolation and Message Analysis

Cells were grown to ~80% confluence. Total RNA was isolated using the RNAzol B reagent (TEL-TEST Inc). A standard Northern hybridization protocol was used for total RNA analysis. In brief, 30 µg total RNA or 10 µg oligo-dT-binding RNA from each cell line was eletrophoresed through a 1% agarose/7% formaldehyde gel. RNA was transferred to a Nitropur nitrocellulose membrane (MSI Micron Separation Inc) by capillary transfer and fixed by baking (2 hours at 80° C.). Probes were radiolabeled using hexanucleotide random primers in the presence of $[\alpha\text{-}^{32}P]$-dCTP to a specific activity of $>10^8$ cpm/µg DNA. cDNA clones for human tissue inhibitors of metalloproteases-1 and tissue inhibitors of metalloproteases-2 were obtained from Dr. Unnar Thorgeirsson (NIH).

Figure 1B:
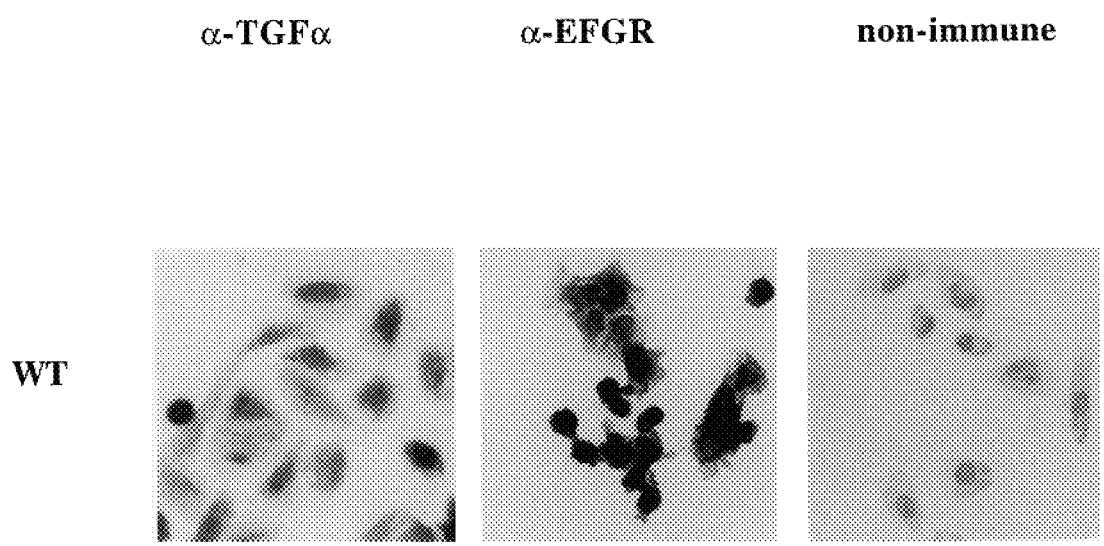
Figure 1C:
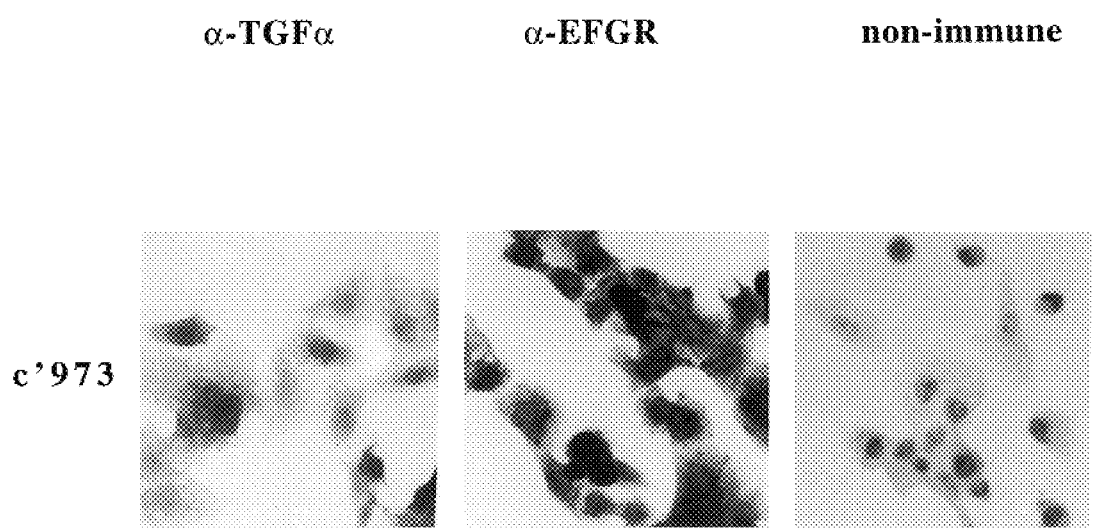

EXAMPLE 10
Epidermal Growth Factor Receptors were Expressed on Parental and Infectant DU-145 Cells The presence of both transforming growth factor-α and its receptor, epidermal growth factor receptor, was determined in Parental and infectant DU-145 cells (FIGS. 1A–1C). Cells were plated on glass coverslips under conditions which minimized receptor-ligand internalization and degradation [49, 50]. Immunohistochemical staining detected transforming growth factor-α in all three sublines (FIGS. 1A–1C), confirming previous reports of DU-145 cells producing transforming growth factor-α [28, 29]. A monoclonal antibody directed against an epitope in the extracellular ligand-binding domain of epidermal growth factor receptor revealed homogenous epidermal growth factor receptor expression in all three cell lines (FIGS. 1A–1C), as expected after retroviral transduction [39, 41].

Figure 2A:
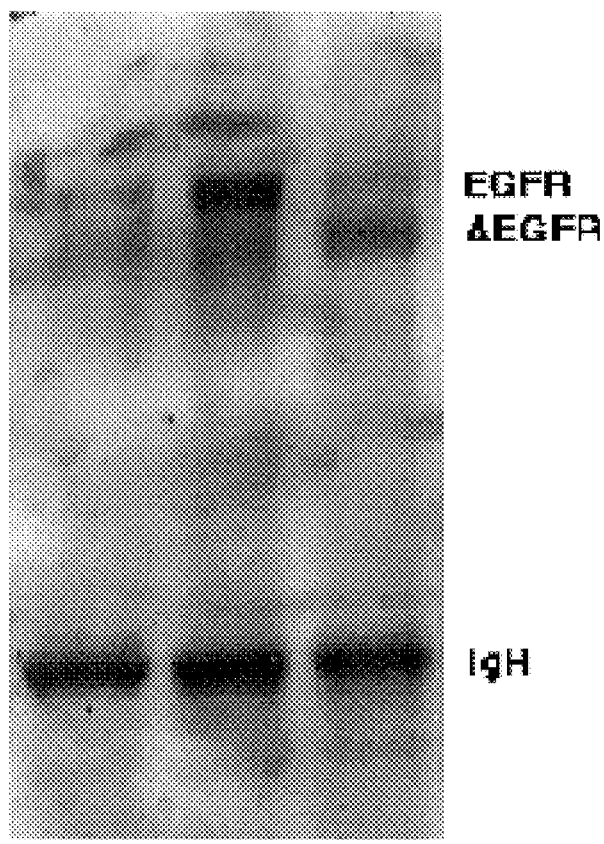
FIG. 2 shows the epidermal growth factor receptor expression in the DU-145 sublines. Cells were analyzed under conditions in which autocrine down-regulation was allowed to occur (FIG. 2A) or minimized and endosomal degradation blocked by methylamine (FIG. 2B). Epidermal growth factor receptor were immunoprecipitated from Parental (P) cells and wild type and c'973 cells using a monoclonal antibody against the extracellular domain (Mab 528 [45]). The immunoprecipitates were separated by 7.5% SDS-PAGE, and detected by immunoblotting with a second antibody (Oncogene Sciences, LA22). Endogenous and wild type epidermal growth factor receptor are denoted at ~175 kDa, with a minor amount being the calpain-hinge cleaved version which migrates slightly faster (~150 kDa) [52, 53]. The truncated c'973 epidermal growth factor receptor, being 213 amino acids shorter, migrates at ~150 kDa. IgH refers to the heavy chain of the immunoprecipitating antibody.

The co-expression of transforming growth factor-α and epidermal growth factor receptor would be expected to downregulate the epidermal growth factor receptor in these cells. Epidermal growth factor receptor were detected by immunoprecipitation followed by immunoblotting, while cultured under conditions of normal cell growth, during which epidermal growth factor receptor downregulation would proceed (FIG. 2A). The carboxy-terminal truncated epidermal growth factor receptor is 213 amino acids shorter, and migrates as a ~25 kDa smaller protein in SDS-PAGE [51]. Epidermal growth factor receptor were barely detectable in the Parental cells. The WT cells presented significantly more full-length epidermal growth factor receptor mass than the Parental line (FIG. 2A). Thus, full-length epidermal growth factor receptor are not down-regulated and degraded to the same extent in the WT cells, presumably due to the combined production from the endogenous and exogenous epidermal growth factor receptor genes exceeding the endocytic capacity [49]. Though limited epidermal growth factor receptor degradation was noted by the presence of the calpain hinge-cleaved product at ~150 kDa [52, 53]. As the transduced WT epidermal growth factor receptor migrates identically to endogenous receptor, the source of the epidermal growth factor binding sites presented on the WT cells could not be ascertained with certainty. However, RNA analysis demonstrated that there was epidermal growth factor receptor message from the transduced gene. The majority of the epidermal growth factor receptor on the c'973 cells was the transduced epidermal growth factor receptor migrating at ~150 kDa (FIG. 2A). This is most likely the consequence of c'973 being resistant to ligand-induced down-regulation [39] due to removal of internalization domains [51]. Importantly, the level of full-length (endogenous) epidermal growth factor receptor, at ~175 kDa, was decreased in this line.

Figure 2B:
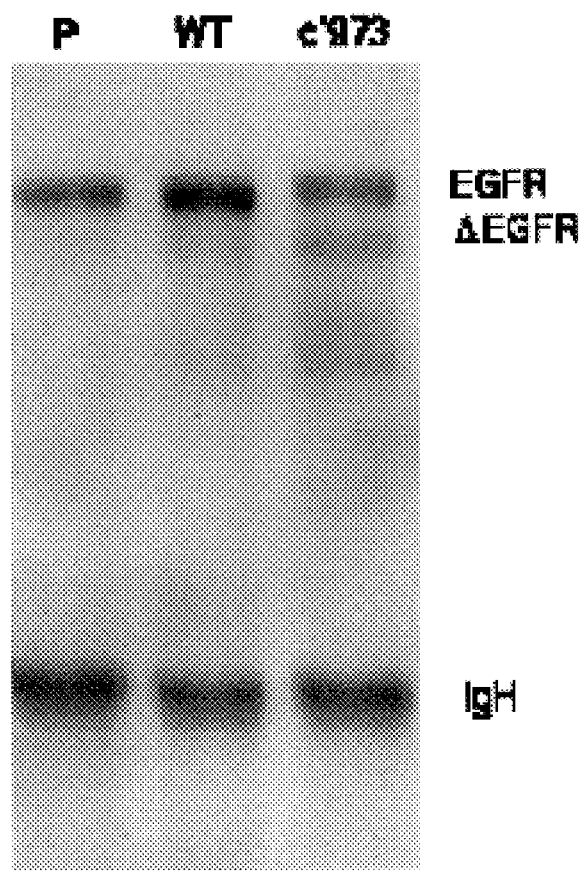

Minimization of epidermal growth factor receptor down-regulation by cell plating in the absence of trypsin, extensive washing, and brief (~12 hours) recovery period, coupled with inhibition of degradation by methylamine (30 nM) [49, 54], demonstrated that all three sublines produced epidermal growth factor receptor (FIG. 2B). In the c'973 cells, both the endogenous full-length receptor and transduced truncated receptor were noted. Under these conditions which promote accumulation of epidermal growth factor receptor on the cell surface, differences in epidermal growth factor binding capacity were seen by scatchard analyses of these cells after removal of bound endogenous ligand. WT and c'973 cells presented significantly more binding sites (136% and 196%, respectively) than the Parental cells. Epidermal growth factor receptor on all three sublines had similar $K_d$ values (ranging from 0.6 to 0.9 nM). These results are in accordance with the relative levels seen by immunoblotting (FIG. 2B). In sum, all three lines produced both ligand and receptor, allowing for autocrine signaling.

Figure 3:
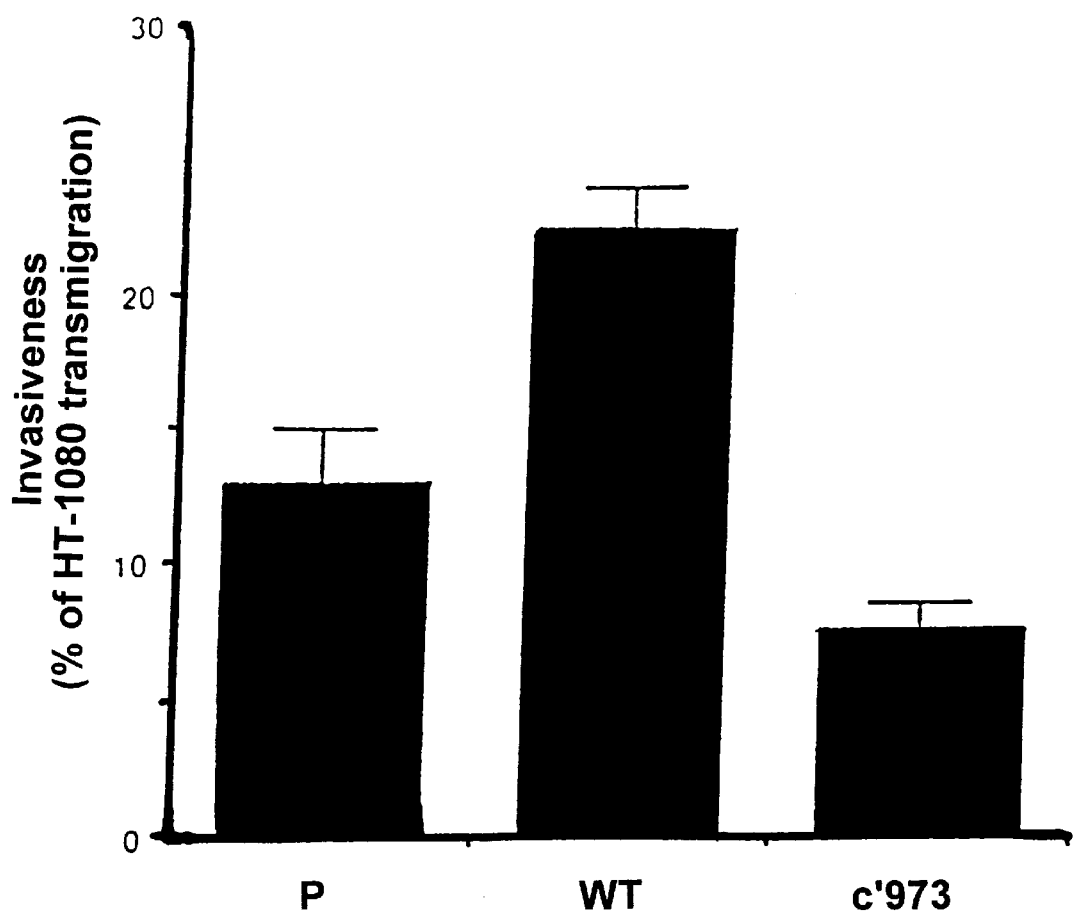
FIG. 3 shows the invasion through an extracellular matrix. The Parental (P) and wild type (WT) and c'973 cells were tested for the ability to transmigrate a human extracellular matrix, Amgel. The invasiveness of each line was determined as a percentage of a highly invasive human fibrosarcoma-derived line, HT1080. Shown is the mean±s.e.m. of three independent experiments each performed in quadruplicate; $P<0.01$ comparing between each pair of cell lines. This demonstrates that tumor cell invasion is dependent on signals from the phospholipase C-activating domain of the epidermal growth factor receptor.

EXAMPLE 11
Cells Expressing Wild Type EGFR Transmigrated a Human Extracellular Matrix to a Greater Extent than those Expressing the c'973 EGFR Parental and infectant lines were tested for the ability to transmigrate a human extracellular matrix, Amgel [38]. If epidermal growth factor receptor signaling contributed to invasiveness then WT cells would be expected to demonstrate enhanced transmigration, as epidermal growth factor receptor were downregulated to a lesser extent than those on the Parental cells. FIG. 3 shows that WT cells transmigrates the extracellular matrix significantly better than Parental cells (1.75±0.22-fold on average). c'973 Cells served to determine if specific receptor domains were required for epidermal growth factor receptor-mediated invasiveness. This truncated receptor lacks the unique carboxy-terminus of the epidermal growth factor receptor and all autophosphorylation sites, but is fully mitogenic [36, 39, 55]. The cells expressing the c'973 epidermal growth factor receptor demonstrated diminished invasiveness compared to the parental cells (0.62±0.23-fold on average) (FIG. 3).

These differences in cell invasiveness were noted in the absence of exogenous epidermal growth factor or transforming growth factor-α. Unlike EHS tumor-derived Matrigel, Amgel does not contain detectable levels of epidermal growth factor or transforming growth factor-α [38]. However, all three cell sublines do produce transforming growth factor-α (FIGS. 1A–1C). Furthermore, the differences in invasiveness were not due to differences in cell proliferation for two reasons. First, in a parallel assay, the three sublines proliferated at equal rates when grown on plastic, i.e., at three days the cell numbers were 386±16%, 380±48%, and 360±26% of initial cell number for Parental, WT, and c'973 cells, respectively (n=2, each experiment contained 8 points). Second, even if there was differential cell proliferation while on the Amgel matrix, this would not affect the determination of the percent transmigration, as the percent of applied is measured, acid-precipitable (i.e. incorporated) label which appears in the lower chamber.

EXAMPLE 12
In Vitro Invasiveness was Inhibited by Anti-EGFR Antibodies

Figure 4:
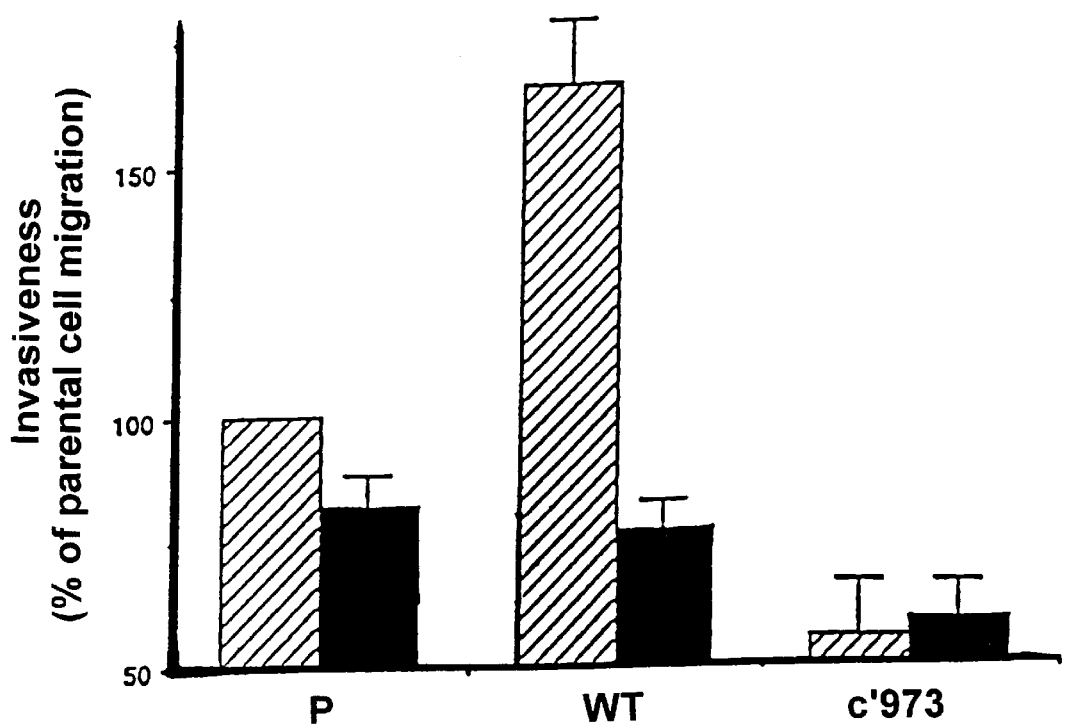
FIG. 4 shows the inhibition of invasiveness by an anti-epidermal growth factor receptor antibody. Parental (P) and wild type (WT) and c'973 cells were tested for Amgel invasiveness in the presence of 4 µg/ml of murine IgG (control) (hatched bars) or a non-activating monoclonal antibody (Mab 528 [45]) (filled bars) which is a competitive inhibitor of ligand binding. Invasiveness is presented as percent of Parental cells. The change in cell invasiveness (mean±s.e.m.) in the presence of the anti-epidermal growth factor receptor antibody is shown for four independent experiments each performed in quadruplicate. $P<0.01$ for anti-epidermal growth factor receptor treated P and WT cells compared to their controls; $P>0.10$ comparing c'973 to its control and comparing anti-epidermal growth factor receptor treated P to anti-epidermal growth factor receptor treated WT cells.

If epidermal growth factor receptor-mediated signaling contributed to invasiveness, then blocking epidermal growth factor receptor activation should reduce the epidermal growth factor receptor dependant transmigration of the Amgel matrix. Addition of a non-activating monoclonal antibody which blocks ligand binding [45] diminished the effect of transduced epidermal growth factor receptor (FIG. 4). The anti-epidermal growth factor receptor monoclonal antibody inhibited invasiveness by WT cells to the greatest extent (transmigration decreased by 54±4%). Invasiveness by Parental cells was also significantly reduced (18±8%). Transmigration of the Amgel by c'973 cells was unaffected by the anti-epidermal growth factor receptor antibody and the slight increase (7±12%) was not distinguishable from control IgG alone. In the presence of the anti-epidermal growth factor receptor antibody, the levels of invasiveness of the three sublines were statistically similar. These data further support the epidermal growth factor receptor-dependancy of the increased invasiveness.

The anti-epidermal growth factor receptor antibody reduced cell proliferation in all three sublines to a similar extent. In parallel assays of cells cultured on plastic for three days, cell numbers in the presence of the anti-epidermal growth factor receptor antibody were 38±4%, 33±12%, and 42±16% of untreated, control cells for Parental, WT, and c'973 cells, respectively. Furthermore, as the incorporated label in the lower chamber is measured, the percent transmigration is independent of cell proliferation. However, as cell death could result in spuriously lower levels of acid-precipitable label appearing in the lower chamber, it was determined if antibody treatment increased cell death. Using the terminal deoxy-transferase (Apoptag Kit, Oncor) method, presence of 4 μg/ml of the anti-epidermal growth factor receptor antibody only marginally increased the very low levels of cell death at three days; Parental cells: 1.1±0.3% in controls to 3.4±1.6% in treated, WT cells: 1.6±1.1% to 2.0±1.1%, and c'973 cells: 3.4±1.6% to 5.0±1.0% (n=2, each in triplicate with no statistically significant different between the cell lines or epidermal growth factor treatment). Interestingly, the WT cells, invasiveness of which was inhibited to the greatest extent (FIG. 4), presented the lowest level of cell death.

EXAMPLE 13
Collagenolytic Activities of the Cell Lines do not Correlate with Invasiveness Transmigration of extracellular matrix is considered to be dependent on three cell properties: matrix recognition, proteolytic extracellular matrix remodeling and degradation, and active movement through the resultant defect. Previously, it was demonstrated that epidermal growth factor receptor signaling enhances NR6 cell motility via activation of PLCγ [37]. Autophosphorylated tyrosines in the carboxy terminus of the epidermal growth factor receptor are required for enhanced cell motility [36]. Thus, WT epidermal growth factor receptor but not c'973 epidermal growth factor receptor enhanced cell motility. This effect on cell motility parallels the results of transmigration of the DU-145 sublines. However, proteolytic activity is a necessary precursor for invasion. It was asked whether the DU-145 sublines secreted different levels of extracellular matrix-degrading metalloproteases; focusing on collagenolytic activity, as assessed by gelatin zymography, as collagen types I and IV are the major constituents of Amgel [38].

Figure 5A:
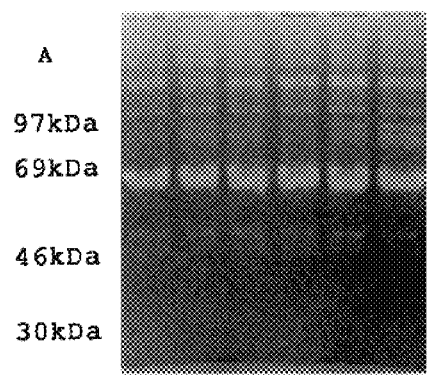
FIG. 5 shows the Gelatinase activity produced by DU-145 sublines. Cells were plated on plastic and quiesced in 1% dFBS for 36–48 hours. Secreted collagenolytic activity was collected from 0 to 14 hours of incubation (FIG. 5A & FIG. 5B) or from 34 to 48 hours (FIG. 5C & FIG. 5D). The cells were incubated in the absence (−) or presence (+) of epidermal growth factor (10 nM) during the entire incubation period. Equal amounts of protein from each cell subline and condition were analyzed by zymography using acrylamide gels containing gelatin alone (0.15%) (FIG. 5A & FIG. 5C) or in conjunction with plasminogen (1 µg/ml) (FIG. 5B & FIG. 5D). Shown are representative zymograms; repeat zymograms with greater or lesser amounts of protein have been utilized to evaluate individual bands within the linear range of the assay. Each series of experiments was performed independently at least three times.
Figure 5B:
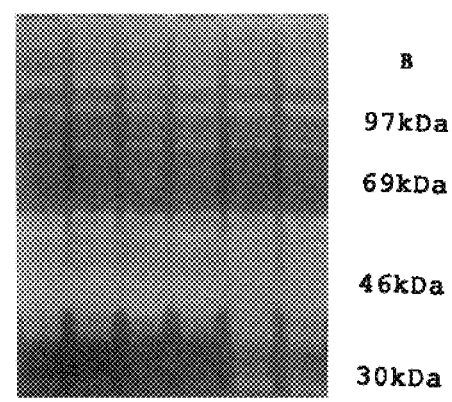

The secreted levels of the MMP-9 (92 kDa gelatinase) and MMP-2 (72/64 kDa gelatinase) were assessed by zymography (FIG. 5). These two collagenases preferentially degrade collagen type IV, and are more frequently associated with tumor invasion and metastasis than other metalloproteases [56, 57]. All three DU-145 sublines secreted near equivalent amounts of these enzymes (FIG. 5A). Addition of exogenous epidermal growth factor had no discernable effect on the levels of enzyme activities. Control experiments in which the amount of sample applied was varied demonstrated that a 10% difference could be distinguished. Metalloproteases are secreted as pro-enzymes and are complexed with inhibitors. It was possible that the cell lines initially secreted different levels of pro-enzymes. Therefore, first activated was the metalloproteases with APMA but did not note significant differences in protease activities. Immunoblots using monoclonal antibodies to detect mass levels of MMP-9 and MMP-2 also demonstrated that WT cells expressed equal or slightly lower levels of these collagenases when compared with the less invasive Parental and c'973 cells.

The addition of plasminogen to the zymogram (FIG. 5B) revealed the presence of plasminogen-dependent protease activity in all the lines. The major collagenolytic activity in the presence of plasminogen appears at ~50 kDa, consistent with identification as urokinase-type plasminogen activator [58]. Interestingly, the Parental and c'973 cells secreted more plasminogen-dependent activity than the more invasive WT cells.

The Amgel invasion assay was performed over a 72 hr period. Therefore, the proteolytic activity secreted between 0–14 hours and 34–48 hours was determined, corresponding to early and late responses, respectively. No differences in proteolytic activities were noted between these two time periods (FIGS. 5C & 5D). In no situation was noted a significant epidermal growth factor effect on secreted activity. This was not unexpected as these cells produce transforming growth factor-β and possess a functional autocrine loop.

EXAMPLE 14
Cells Cultured on Extracellular Matrix Secreted Proteases in a Pattern Which Did Not Correlate to Invasiveness The initial series of zymograms (FIG. 5) investigated secretion of proteases while cells were seeded on plastic. In such a situation, the components of the cell matrix are produced by the cells and derived from the FBS. Signaling from matrix components is a well-documented, widespread phenomenon. Matrix constituents also affect tumor cell growth [59] and metastasis [60, 61]. Because the invasiveness of a biologic extracellular matrix, Amgel, had been measured it was necessary to determine whether components in the matrix signaled protease production.

Figure 6B:
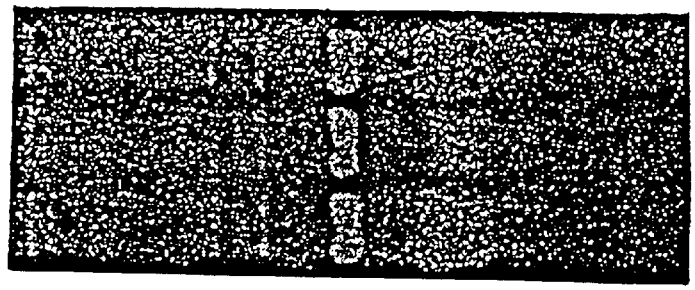
FIG. 6 shows the Gelatinase activity produced by DU-145 sublines cultured on Amgel. Cells were plated on Amgel-coated (4 mg/ml) plates, and treated as described below and the legend to FIG. 5. Collagenolytic activity was collected from 0 to 14 hours (FIG. 6A & FIG. 6B) or from 34 to 48 hours (FIG. 6C & FIG. 6D). Equal amounts of protein from each cell line subline were analyzed in gels copolymerized with gelatin (FIG. 6A & FIG. 6C) or in conjunction with plasminogen (FIG. 6B & FIG. 6D). Shown are representative zymograms; repeat zymograms with greater or lesser amounts of protein have been utilized to evaluate individual bands within the linear range of the assay. Each series of experiments was performed independently three times for the 0 to 14 hour period and twice for the 34 to 48 hour period. Data represented in FIGS. 5 and 6 demonstrate that changes in protease levels are not the major determinants of DU-145 prostate tumor cell invasiveness in vitro.

Cells were seeded onto Amgel-coated dishes, similarly to the invasion assay. Conditioned media was collected from either the 0–14 hours (FIGS. 6A & 6B) or 34–48 hours (FIGS. 6C & 6D) time periods, and analyzed as with the cells seeded onto plastic. The pattern of collagenases was similar between the cells on Amgel and those on plastic. Neither activation by APMA (data not shown), nor presence of plasminogen (FIGS. 6B & 6D) caused differences from the enzyme patterns seen with cells on plastic. Comparisons between the cell lines revealed excess protease activity in the Parental and c'973 cells, not in the more invasive WT cells.

Figure 7:
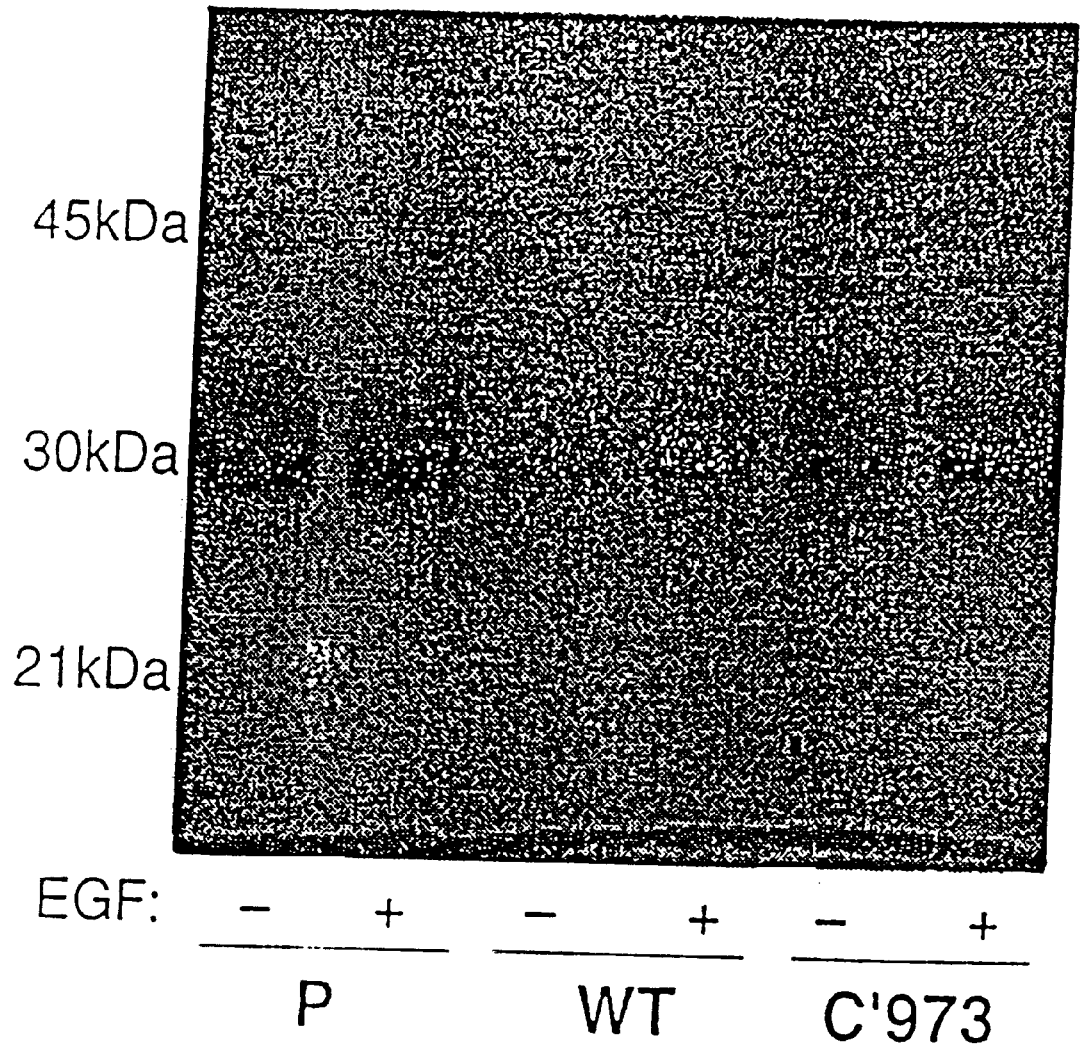
FIG. 7 shows the production of tissue inhibitors of metalloproteases-1 by DU-145 sublines. Parental (P), WT and c'973 cells were plated on plastic, quiesced in 1% dFBS, and treated for 14 hour in the absence (−) or presence (+) of epidermal growth factor (10 nM). Equal amounts of secreted protein (15 µg) were analyzed by immunoblotting for presence of tissue inhibitors of metalloproteases-1. A representative immunoblot is shown; a similar pattern was noted in an second independent experiment.

EXAMPLE 15
Levels of Tissue Inhibitors of Metalloproteases (TIMP)-1 Did Not Correlate Inversely with Invasiveness Total proteolytic activity is a balance between proteases and their inhibitors. Tissue inhibitors of metalloproteases-1 and -2 are produced by many transformed cells. Tissue inhibitors of metalloproteases-1 binds stoichiometrically to all MMPs but preferentially inhibits MMP-9; tissue inhibitors of metalloproteases-2 preferentially inhibits MMP-2 [57, 62]. Reverse zymography is used to detect collagenase inhibiting proteins. Such inhibitors secreted by the DU-145 sublines could not be detected using this technique and production was assessed by analyzing protein mass and message levels. Immunoblotting detected tissue inhibitors of metalloproteases-1, but not tissue inhibitors of metalloproteases-2 (FIG. 7). The level of tissue inhibitors of metalloproteases-1 present in the media was increased by treatment of the cells with epidermal growth factor in the WT and c'973 cells. Epidermal growth factor treatment did not alter levels in the Parental cells which presented the highest level of tissue inhibitors of metalloproteases-1 as Parental cells still demonstrated invasiveness. Tissue inhibitors of metalloproteases-1 and -2 mRNA levels also were ascertained in cells grown under conditions which minimized autocrine stimulation. Total RNA or oligo-dT chromatography-enriched RNA was hybridized with probes specific for human tissue inhibitors of metalloproteases-1, -2, and γ-actinin (the latter to control for mRNA abundance). Relative quantitations were performed by phosphor-image analyses (Molecular Dynamics). Tissue inhibitors of metalloproteases-1 message levels were slightly higher in c'973 cells than in Parental cells (Parental:WT:c'973 were 1.07±0.14:0.54±0.10:1.34±0.29, relative to γ-actinin (n=3). Tissue inhibitors of metalloproteases-2 message levels demonstrated the opposite pattern, though at about 20% the level of tissue inhibitors of metalloproteases-1 message (Parental:WT:c'973 were 0.21:0.24:0.17; relative to γ-actinin; n=1). Epidermal growth factor exposure resulted in slightly increased tissue inhibitors of metalloproteases-1 levels and similar, slightly decreased tissue inhibitors of metalloproteases-2 message levels.

Upregulated signaling of the epidermal growth factor receptor system has been correlated with tumor cell invasion and metastasis [14–21, 23]. The extent of invasiveness of DU-145 human prostate carcinoma cells can be modulated by epidermal growth factor receptor expression. Cells expressing elevated levels of full-length (WT) epidermal growth factor receptor invaded through an extracellular matrix to a greater extent than Parental cells. A monoclonal antibody which prevents ligand binding and subsequent epidermal growth factor receptor activation inhibited the transmigration of these cells. This suggests that epidermal growth factor receptor signaling, probably secondary to transforming growth factor-α-induced autocrine stimulatory loop, promoted invasiveness.

Whether endogenous epidermal growth factor receptor signaling contributes to invasiveness of Parental DU-145 cells was also examined. Epidermal growth factor receptor signal blockade by a monoclonal antibody decreased the invasiveness of these cells by 20%. This finding is distinct from blocking invasiveness enhanced by exogenous ligand [23], in that signals intrinsic to the DU-145 cells are promoting invasiveness. These data, coupled with the fact that the monoclonal antibody inhibited invasiveness of both Parental and WT cells down to a similar level, suggests that a component of DU-145 invasiveness is epidermal growth factor receptor-mediated secondary to autocrine stimulation.

A kinase-active, mitogenesis-competent truncated epidermal growth factor receptor (c'973) [36, 39] is expressed in the DU-145 cells. Cells expressing this truncated receptor were significantly less invasive than Parental cells (FIG. 3), even though they expressed more epidermal growth factor binding sites and receptor mass. The reduced invasiveness could be secondary either to transmittal of a signal antagonistic to invasiveness such as decreasing extracellular matrix recognition, or down-regulation of signaling from the endogenous full-length epidermal growth factor receptor. If it were the former, then the blocking antibody would be expected to increase the invasiveness of c'973 cells. In fact, these cells transmigrated the extracellular matrix similarly in the absence or presence of blocking antibody (FIG. 4). Thus, c'973 signaling does not contribute to cell invasiveness. The presence of the c'973 epidermal growth factor receptor likely results in decreased signaling from the endogenous full-length epidermal growth factor receptor in these cells (FIG. 2A). It is proposed that signaling domains in the carboxy-terminus of the epidermal growth factor receptor are required for epidermal growth factor receptor-mediated invasiveness. The level of invasiveness exhibited by c'973 cells represents the basal invasiveness of DU-145 cells in the absence of epidermal growth factor receptor signaling.

The mechanism(s) by which epidermal growth factor receptor signaling enhances invasiveness is unknown. Epidermal growth factor receptor signals have been implicated in modulating cell phenotypes which control all three aspects of invasiveness. It has been shown that epidermal growth factor causes cells to retract lamellipodia and decrease attachment acutely, and that this effect occurs in cells which express both WT and c'973 epidermal growth factor receptor [41]. While these signaling responses must be confirmed in DU-145 cells using Amgel as the attachment matrix, the fact that antibody exposure of c'973 cells does not enhance invasiveness, suggests that differences in matrix recognition are not the underlying mechanism of EGF-receptor-mediated invasiveness.

Epidermal growth factor-induced cell motility is dependent on phosphotyrosine motifs in the carboxy-terminus of the receptor [36, 37]. WT, but not c'973 epidermal growth factor receptor, when expressed in NR6 cells signaled enhanced cell motility. This could account for the difference in invasiveness between WT and c'973 cells. The enhanced invasiveness shown by WT cells when compared to Parental cells may be explained through the higher level of epidermal growth factor receptor in the WT cells (FIG. 2). Partial inhibition of PLCγ signaling in the transduced NR6 cells by pharmacologic and molecular agents [37] resulted in an activity-dependent decrease in cell motility. Thus, differences in epidermal growth factor receptor level and overall signaling may result in differential motility.

Figure 6:
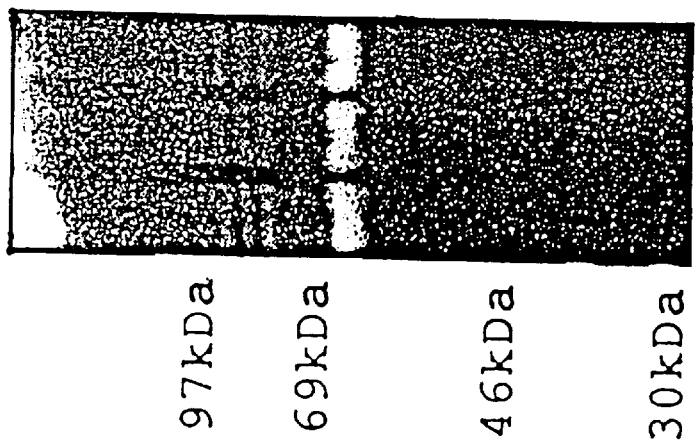
Figure 6D:
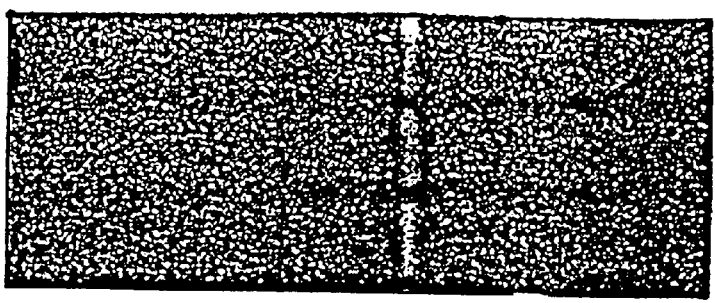
Figure 6C:
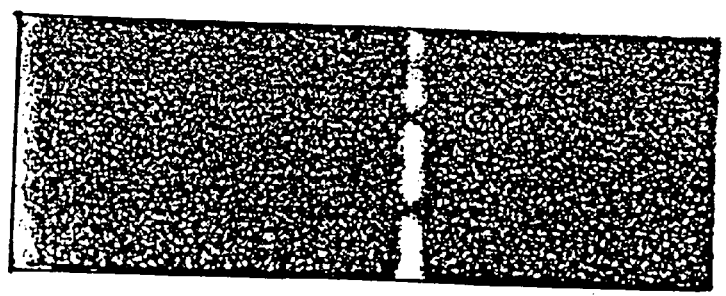

Proteolytic degradation is required for transmigration of an extracellular matrix. Differential protease production would be expected to result in differing invasiveness. Epidermal growth factor has been shown to increase levels of a number of different proteases [3, 32, 33]. Whether epidermal growth factor receptor-mediated invasiveness was accomplished through this mechanism was examined and initially, type IV collagenase production was focused on. Zymograms were utilized to determine total collagenolytic activity secreted into the media, and avoid the problems in the interpretation of transcription, translation, and post-translational regulation events. WT cells demonstrated equivalent or lesser levels of collagenases than the less invasive Parental or c'973 cells whether on plastic or on Amgel (FIGS. 5 & 6). In an additional series of investigations, it was not noted that greater casein degradation as measured by casein-based zymography to detect non-collagen-directed proteolysis, in the more invasive WT cells (data not shown).

Collagenolytic activity is a balance between collagenases and tissue inhibitors of metalloproteases species. Collagenase inhibitory activity by reverse zymography could not be demonstrated. Therefore, production of the two major collagenase inhibitory species was assessed by protein mass and message levels. Tissue inhibitors of metalloproteases-1 was found to be produced by all three sublines, with WT cells expressing less than the other sublines (FIG. 6). However, relative tissue inhibitors of metalloproteases-1 production (Parental>c'973>WT) paralleled protease production and was not the inverse of invasiveness (WT>Parental>c'973), as would be expected if this was the underlying mechanism for epidermal growth factor receptor-mediated invasiveness. Relative message levels did not parallel the protein mass measurements and whether this is due to differential translation controls or protein consumption or sequestration is unknown. Collagenases and tissue inhibitors of metalloproteases species bound to the cell surface [5, 7] were not detected in the zymography and immunoblot assays for secreted proteins.

In summary, epidermal growth factor receptor-mediated invasiveness of DU-145 does not correlate with increased collagenolysis of specific matrix components. This is not to say that proteolytic degradation of the matrix is not important for invasion and metastasis, as many reports attest to its requirement in this complex process. It is likely that all three sublines produced sufficient proteolytic activity that this was no longer a limiting factor for invasiveness. However, the findings support the contention that tumor cell invasiveness and metastasis involves cell properties in addition to proteolytic degradation of matrix [63].

EXAMPLE 16

Animals

Male athymic BALB/c nu/nu mice were purchased from the Animal Production Area of the National Cancer Institute-Frederick Cancer Research and Development Center (Frederick, Md.). The mice were housed in laminar flow cabinets under specific-pathogen-free conditions. Mice were used at 6–8 weeks of age, and weighed 20 to 27 gm. Animals were maintained in accordance with established institutional guidelines and approved protocols.

EXAMPLE 17

Tumor Cell Inoculations

For intraprostate injections, mice were anesthetized with ketamine hydrochloride/xylazine hydrochloride and placed in the supine position. Methoxyflurane (Pittman-Moore, NJ) was used as an inhalation anesthetic during surgical procedures. The abdomen was cleaned with alcohol and betadyne; a lower midline incision was made and one lobe of the anterior prostate gland was exposed for injection. Tumor cells ($2\times10^6$) resuspended in $Ca^{2+}$-free and $Mg^{2+}$-free Hanks' balanced salt solution (total volume, 20 $\mu l$; HBSS, GIBCO, NY) were injected into one lobe of the anterior prostate gland using a 30-gauge needle, a 1-ml disposable syringe, and a calibrated push-button Hamilton dispensing device (Hamilton Syringe Co., NV). A visual localized bleb within the injected prostate was accepted as the indicator of a satisfactory injection. The abdominal wound was initially closed utilizing discontinuous stitches; the skin was closed with stainless steel wound clips (Autoclip; Clay Adams, NJ). Tumor cells ($2\times10^6$) for intraperitoneal injections were suspended in HBSS (total volume, 200 $\mu l$) and injected (26.5-gauge needle, 1-ml disposable syringe) into the peritoneal cavity.

Pharmacologic treatments of tumors were on a q4d schedule starting 4 days after the mice were inoculated with the WT DU-145 tumor cells and continuing until day 44. Agents were dissolved in 10% DMSO in HBSS in a total volume of 100 $\mu l$. Neomycin sulfate was used at 150 $\mu g$/mouse and U73122 was used at 12 $\mu g$/mouse or 24 $\mu g$/mouse, doses below toxic levels but within therapeutic levels (83). U73343 was injected at 12 mg/mouse, consistent with U73122 treatments.

EXAMPLE 18

Necropsy Procedures and Histologic Studies

Mice were killed by $CO_2$-induced hypoxia at various times (intraprostate, 90–120 days; intraperitoneal, 40–50 days). All lobes of the mouse prostate (anterior, ventral and dorsal/lateral), regional lymph nodes (preaortic or axillary), kidneys, spleen, pancreas, liver, lungs and diaphragm (only taken from animals receiving intraperitoneal injections) were fixed in 10% buffered formalin, paraffin embedded, serially sectioned, and stained with hematoxylin and eosin.

EXAMPLE 19
In Vitro Growth Assay

Cell proliferation was evaluated by assessing mitochondrial reduction of 3-(4,5-dimethythiazol-2yl)-2,5-diphenyl tetrazolium bromide (MTT) as described (84), with the following modifications. Cells were plated at 5,000 cells/well in 96-well microtiter plates in 200 ml growth medium (7.5% FBS in Dulbecco's modified Eagle's medium) and allowed to attach for 24 hours. Serum-containing medium was removed and cells were quiesced for 2 days in 0.5% dialyzed FBS in Dulbecco's modified Eagle's medium. For all dose and time course studies using anti-epidermal growth factor receptor, this medium was removed and replaced with 7.5% FBS in Dulbecco's modified Eagle's medium. In addition the following agents were evaluated: neomycin (0.01–1000 $\mu$M), U73122 (0.001–100 $\mu$M) (BIOMOL, PA), and anti-epidermal growth factor receptor antibody (0.001–4 $\mu$g) (AB-1, Oncogene Science, NY). At harvest, medium was removed from the appropriate wells, replaced with 50 $\mu$l of MTT solution (2 mg MTT/ml PBS; Sigma, MO) and incubated for 4 hours at 37° C. After incubation, the MTT solution was carefully aspirated; 100 $\mu$l dimethylsulfoxide (DMSO, Sigma, MO) was added to each well. Data was analyzed on plate reader using the Soft Max program (Molecular Devices Corp., Menlo Park, Calif.).

EXAMPLE 20
Infectant DU-145 Cell Lines Form Tumors in the Prostate and Peritoneal Cavity The tumorigenicity of DU-145 sublines was examined in vivo by injecting 2×10⁶ cells either into one lobe of the anterior prostate (to reflect the in situ situation) or the peritoneal cavity (to recapitulate the initial stages of local invasion) of athymic mice. In intraprostate inoculated animals, an orthotopic site, tumor formation was observed in all DU-145 sublines, though c'973 DU-145 cells formed tumors only at a significantly lower rate. Distinct differences existed between the different cell lines when tumor invasiveness (local and distal) and metastasis (to lung) were examined (TABLE 1A). Only Parental and WT sublines formed large tumors at site of injection (WT>PA>>c'973); c'973 tumors formed in the prostate were restricted to site of injection and were not locally invasive. Local (adjoining seminal vesicle; scored as 3+) and distal (through the capsule and into surrounding tissue; scored as 4+) tumor invasion and metastases (preaortic lymph nodes, pancreas, liver) were evident only in the Parental and WT sublines, though the WT cells invaded to a greater extent. The incidence of macroscopic lung metastases for Parental and WT sublines was similar (50% and 44%, respectively).

TABLE 1

Prostate Tumor Progression by Parental, WT and c'973 Epidermal growth factor receptor-expressing DU-145 Cells

| A. Site | Intraprostate | | |
|---|---|---|---|
| Subline | Tumor formation[a] | Invasiveness[b] | Lung metastases[a] |
| Parental | 11/16 | 3.0 + (0–4) | 8/16 |
| WT EGFR | 9/16 | 3.3 + (2–4) | 7/16 |
| c'973 EGFR | 2/15 | 1.0 + (1,1) | 0/15 |

TABLE 1-continued

Prostate Tumor Progression by Parental, WT and c'973 Epidermal growth factor receptor-expressing DU-145 Cells

| B. Site | Intraperitoneal | | | |
|---|---|---|---|---|
| Subline | Tumor formation[a] | Diaphragm tumors[a] | Diaghragm invasiveness[b] | Lung Metastases[a] |
| Parental | 5/10 | 5/10 | 1.6 + (0–3)[c] | 3/10 |
| WT EGFR | 9/11 | 8/11 | 3.4 + (2–4) | 4/11 |
| c'973 EGFR | 4/11 | 4/11 | 0.5 + (0–2)[c] | |

These numbers are a composite of 3 intraprostate or 2 intraperitoneal inoculations of 5–6 mice per group. a. The number of mice with macroscopic tumors (confirmed by microscopic examination) in the prostate, peritoneal cavity, on the diaphragm surface or in the lungs over the number of mice challenged. b. Invasiveness was scored microscopically on a scale of 0 (non-invasive) to 4 (intraprostate: tumor invading through capsule intosurrounding tissue; intraperitoneal: tumor obliterating the diaphragm); the number is the average invasiveness of all prostate or diaphragm tumors (not including mice which did not present tumors), the range of invasiveness is shown in the parentheses. c. There was no detection of invasion by one of the five Parental DU-145 diaphragm tumors. One of the c'973 DU-145 diaphragm tumors showed 2+ invasiveness; the other three tumors did not invade the diaphragm.

Figure 8:
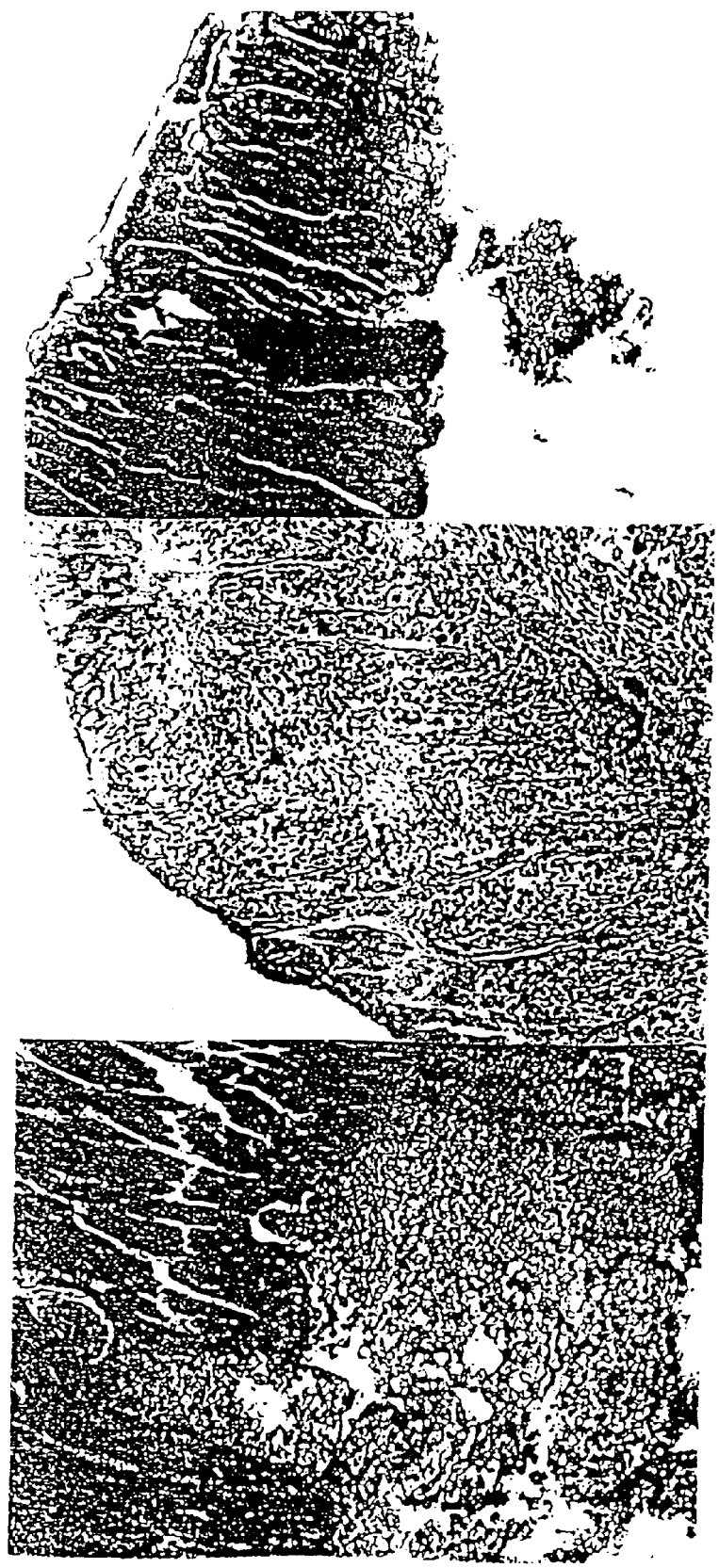
FIG. 8 shows the invasion of Parental (left), WT (center) and c'973 (right) cells into the diaphragm. Mice were inoculated with $2 \times 10^6$ cells in the peritoneal cavity. Mice were euthanized 45 days later, and tumor growth, invasiveness and metastasis determined. Shown are representative tumors on the diaphragmatic surface as a measure of invasiveness. Parental tumors are fixed to the diaphragm with microscopic evidence of invasion, while WT cells have obliterated the diaphragm and have formed lung metastases. c'973 epidermal growth factor receptor cells fail to attach firmly to the diaphragm with no evidence of invasion. The Parental DU-145 tumor is shown at twice the magnification as the other tumors.

Intraperitoneal inoculations were utilized to assess tumor spreading outside of the prostate environment (Table 1B). Again tumors formed in all groups, with the wild type producing the most tumors in various areas of the peritoneal cavity and on the diaphragm serosal surface. Using the extent of tumor invasion into the diaphragm as an indicator of cell invasion (85, 86), DU-145 sublines expressing WT epidermal growth factor receptor were aggressively invasive compared to Parental and c'973 sublines (WT>>PA>>c'973) (FIG. 8). Macroscopic lung metastases were seen only in Parental and WT sublines (30% and 36%, respectively). The greater extent of invasion seen in sublines expressing WT epidermal growth factor receptor in these in vivo models for prostate tumor progression emphasizes the importance of epidermal growth factor receptor in tumor invasion.

Figure 9A:
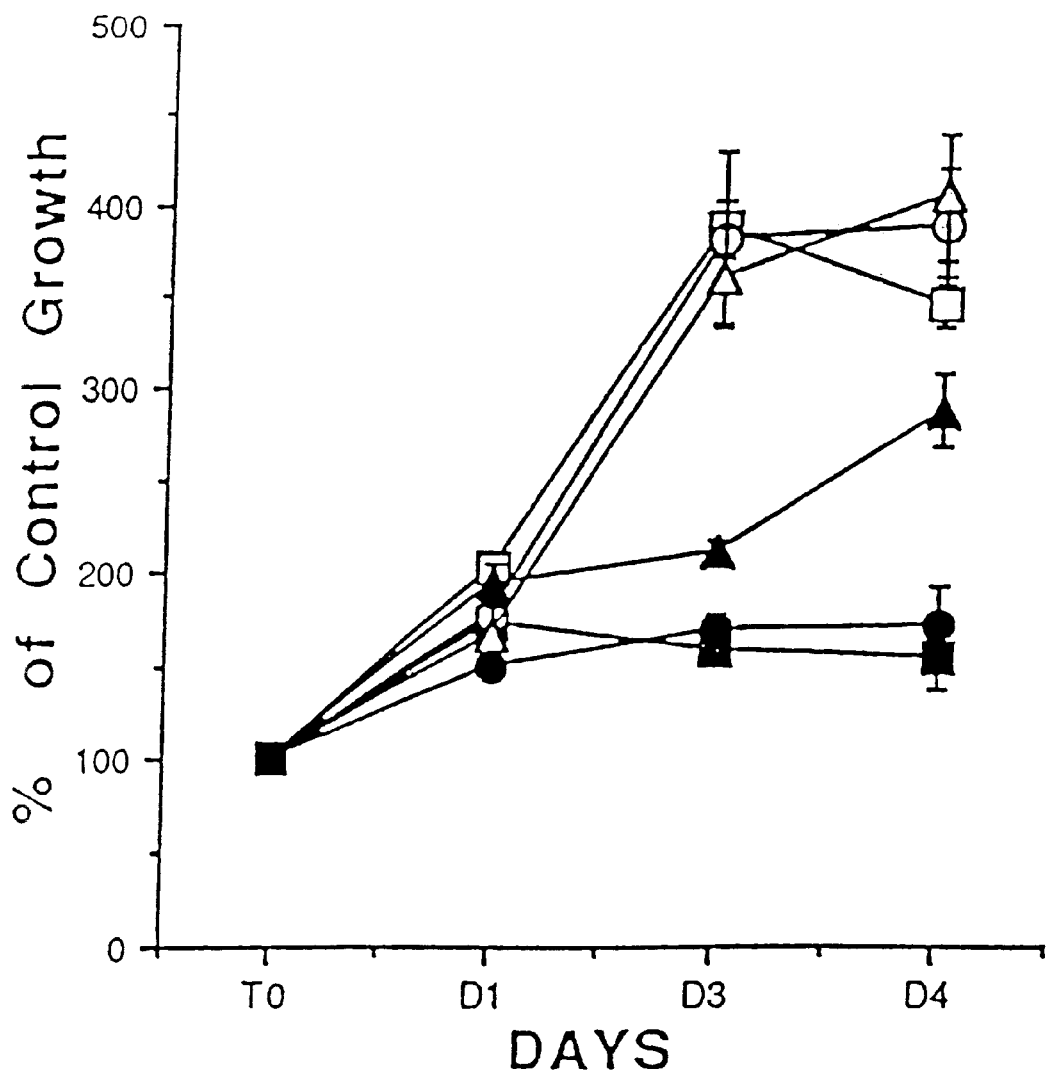
(FIG. 9A) Parental (○) and WT (○) and c'973 (∆) infectant lines were exposed to anti-epidermal growth factor receptor antibody (4 µg/ml) for up to 4 days in the presence of 7.5% FBS. Time Zero (T0) was after 2 days in 0.5% dFBS quiescing medium; this medium was then changed to 7.5% FBS growth medium±4 µg/ml of anti-epidermal growth factor receptor antibody for the duration of the experiment. Open symbols indicate growth medium only; closed symbols indicate the presence of antibody.

EXAMPLE 21
All Three DU-145 Sublines Require an Epidermal Growth Factor Receptor-mediated Autocrine Loop for Cell Proliferation One explanation for the differences found in tumor formation and invasiveness would be differential growth rates of the DU-145 sublines. The cell growth rates in vitro were determined using the MTT dye reduction method. All three sublines grew at comparable rates (FIG. 9A).

Figure 9B:
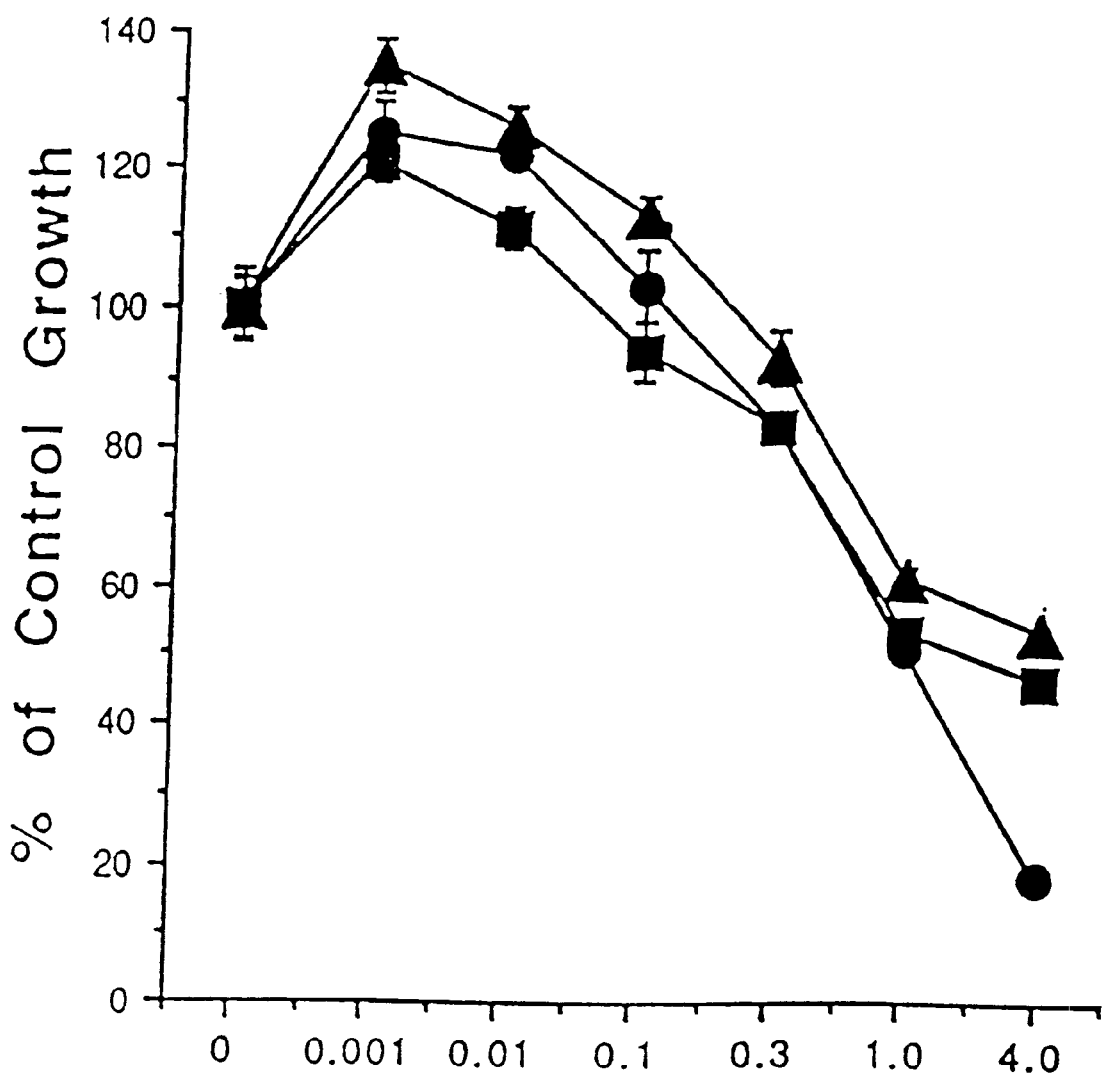
(FIG. 9B) The infectant lines were exposed to various concentrations of anti-epidermal growth factor receptor for 4 days in the presence of 7.5% FBS. Cell growth is expressed as a percentage (mean±s.e.m., n=3) of cells (FIG. 9A) at time 0 (T0) or (FIG. 9B) at day 4 (D4). Medium±antibody was only added at the beginning of the experiments.

These cells both express epidermal growth factor receptor and produce transforming growth factor-α (82). This autocrine stimulatory loop has been shown to be important for promoting in vitro invasiveness as determined by transmigration of human extracellular matrix (82). The importance of this epidermal growth factor receptor-transforming growth factor-α stimulatory loop for cell proliferation was investigated by determining cell proliferation in the presence of a antagonistic anti-epidermal growth factor receptor antibody (45). Anti-epidermal growth factor receptor antibody reduced cell proliferation in all three sublines in a dose dependent manner (FIG. 9B). In parallel studies over a 4 day time-course study using 4 $\mu$g/ml of the anti-epidermal growth factor receptor antibody, a decrease in cell proliferation was observed in all sublines. Inhibition of proliferation was evident in all groups by day 3 (FIG. 9A). Exposure to the anti-epidermal growth factor receptor antibody did not result in reduction of cell number below initial plating density, indicating inhibition of the epidermal growth factor receptor is not from or resulting in cell death. Analysis of sublines exposed to anti-epidermal growth factor receptor antibody for induced apoptotic cell death using the terminal deoxytransferase method (Apoptag Kit, Oncor, MD) showed only marginal levels of apoptotic cell death (<4% of the exposed cells) resulted from the highest concentration of epidermal growth factor receptor antibody (4 µg/ml) (data not shown).

EXAMPLE 22

An Inhibitor of Phospholipase C Activity Reduces Tumor Invasiveness

In vitro invasiveness correlated with the capacity of the epidermal growth factor receptor construct to induce cell motility. That is, the WT epidermal growth factor receptor promotes both proliferation and chemokinesis whereas c'973 induces only proliferation. Epidermal growth factor receptor-mediated cell motility requires phospholipase C (PLC) activity, and can be inhibited by the pharmacologic agent U73122 (1 mM) (BIOMOL, PA) (37). Furthermore, the present invention demonstrates that in vivo invasiveness was promoted by epidermal growth factor receptor-mediated motility signaling and U73122 diminishes tumor invasiveness.

Figure 10A:
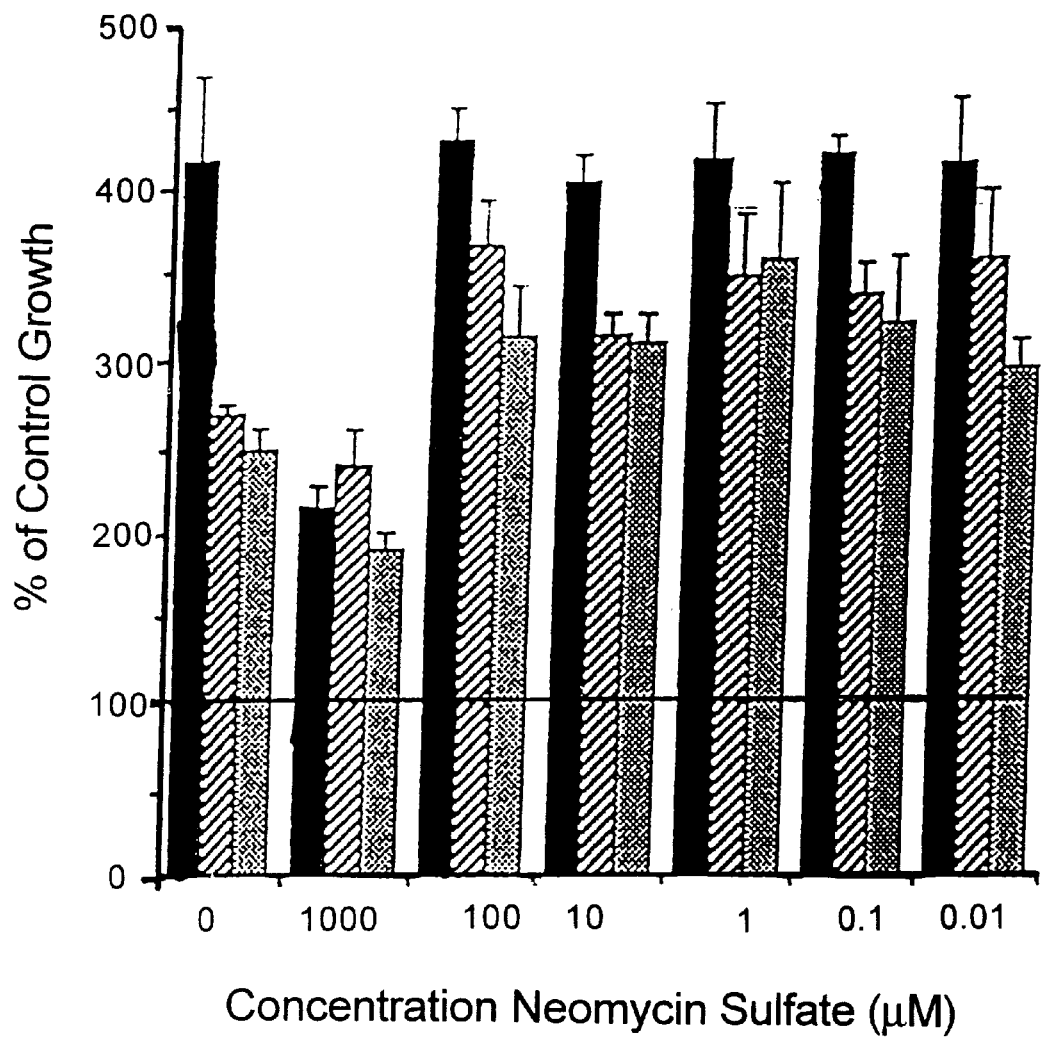
FIG. 10 shows the effects of neomycin sulfate and U73122 on DU-145 cell growth. Parental (filled) and WT (slashed) and c'973 (open) infectant lines were incubated with various concentrations of (FIG. 10A) Neomycin Sulfate (0.01–1000 µM) and (FIG. 10B) U73122 (0.001–100 µM) for 3 days in the presence of 7.5% FBS. Cell growth is expressed as a percentage (mean±s.e.m., n=3) of cells receiving 0.5% dFBS quiesing medium. Medium±pharmacologic agents were only added at the beginning of the experiments.
Figure 10B:
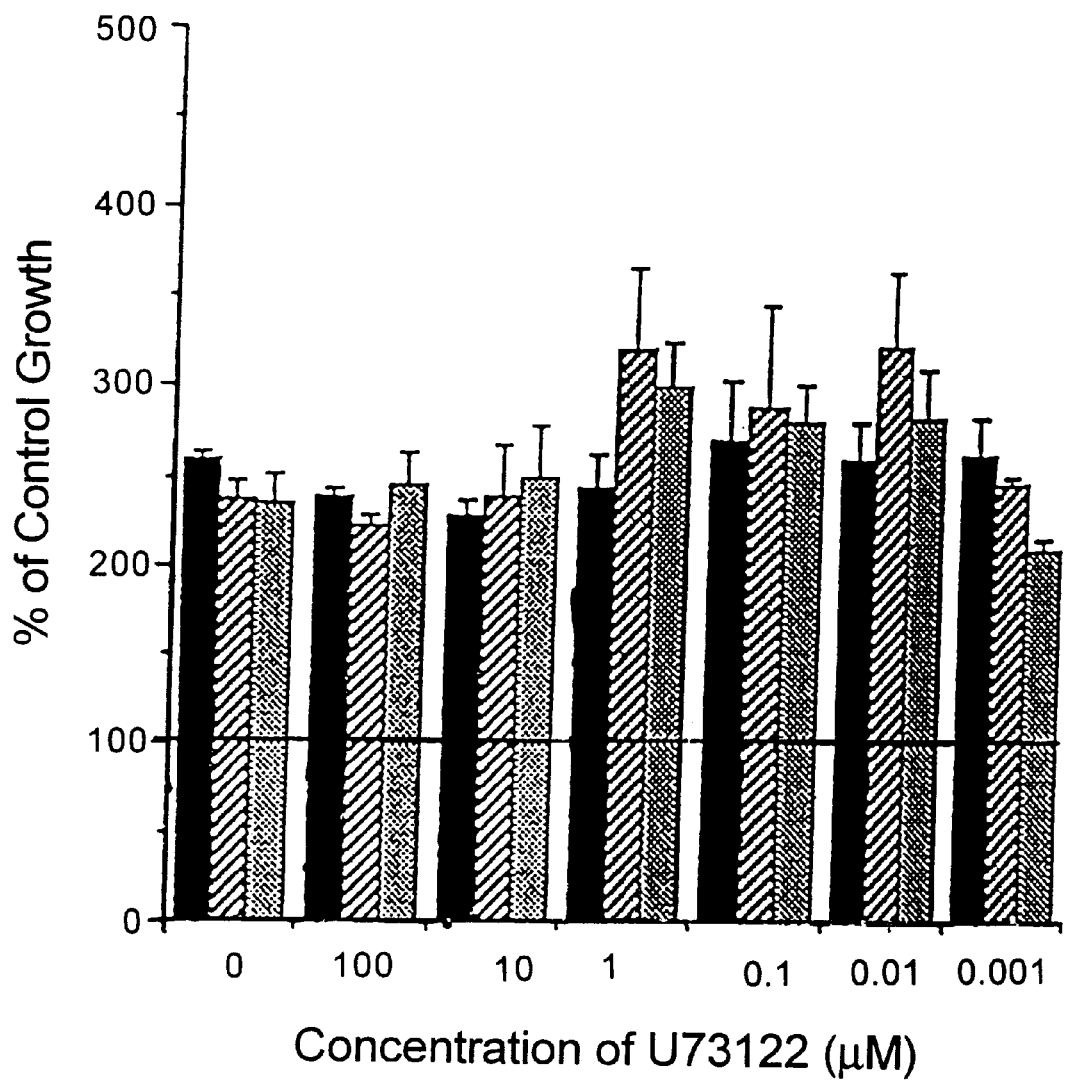

First, the cytotoxicity of U73122 was tested in vitro (FIG. 10). In addition, neomycin was used as a control as it binds to the PLC target phosphoinositide bisphosphate ($PIP_2$). U73122 had no effect on cell proliferation over a three day period, even at doses 100-times greater than that which limits cell motility in NR6 fibroblasts (37). Neomycin sulfate decreased cell proliferation only at the highest concentration tested, but even in this situation there was still significant cell growth over the three day period. These results give further credence to the predicted duality of the epidermal growth factor receptor-mediated motility and mitogenesis pathways (36, 87).

Figure 11A:
FIG. 11 shows the invasion of Control (FIG. 11A and FIG. 11B) and U73122 (FIG. 11C) treated WT DU-145 cells into the diaphragm. Mice were inoculated with $2 \times 10^6$ cells in the peritoneal cavity, and q4 day treatment initiated on day 3. Mice were euthanized 45 days later, and tumor growth and invasiveness determined. Shown are representative tumors on the diaphragmatic surface as a measure of invasiveness. Control-treated cells have obliterated the diaphragm (40× magnification is on left, 100× is in center). U73122 treated cells form tumors which fail to invade the diaphragm (100× magnification).
Figure 11B:
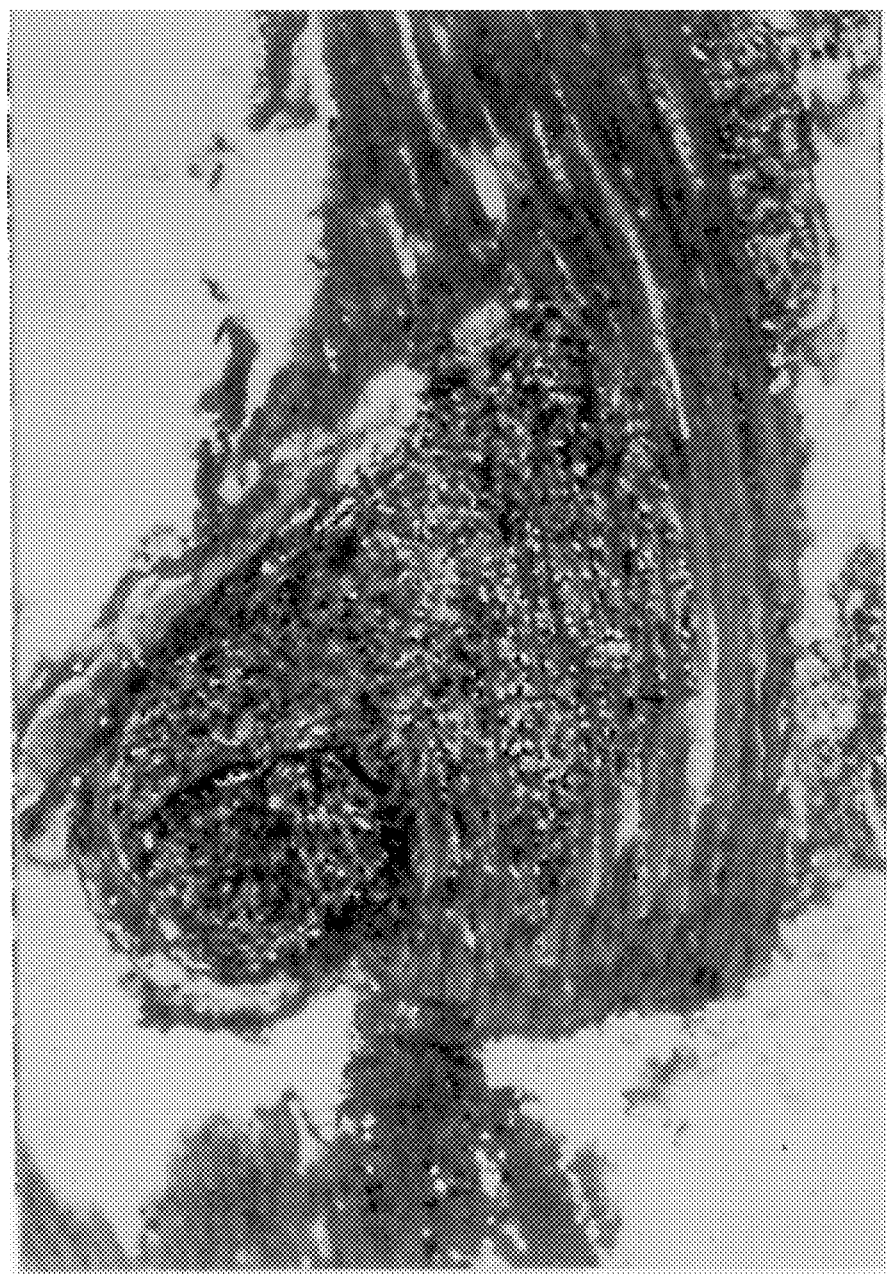
Figure 11C:

The effect of neomycin sulfate and U73122 on prostatic tumor progression was determined in athymic mice bearing intraperitoneal injections of WT DU-145 cells, as this line was the most aggressive. Treatment with neomycin sulfate and U73122 was given to ascertain if the inhibition of PLC in vivo played any role in the inhibition of tumor invasion. The extent of tumor cell penetration into the musculature of the diaphragm serosal surface was the criteria measured. Neomycin sulfate, U73122 or control PBS and U73343 (the inactive congener of U73122) injections were initiated three days post tumor inoculation and continued every 4 days until the experiment was terminated on day 45 (TABLE 2). The WT DU-145 subline formed numerous tumors at several sites, with those on the diaphragm being extremely invasive. Tumor formation within the peritoneal cavity or on the diaphragm occurred in greater than 60% of all treatment groups. Extensive invasion of the diaphragm was observed in control-treated animals (FIGS. 11A–11C). This identical pattern of tumor progression was seen in the neomycin sulfate-treated animals (pictures not shown). In U73122-treated animals, an aggressive pattern of tumor invasion was observed in only one animal. In the other 7 animals presenting tumors on the diaphragm, only initial or negligible tumor cell invasion was observed histologically (FIG. 4); the extent of invasiveness was reduced below that of Parental cells. Thus, the present invention demonstrates that the PLC inhibitor, U73122, inhibits epidermal growth factor receptor-mediated tumor progression.

TABLE 2

Effects of Neomycin Sulfate & U73122 on WT DU-145 Prostate Tumor Progression

| Treatment | Tumor formation[a] | Diaphragm tumors | Diaphragm Invasiveness[b] |
|---|---|---|---|
| Control[c] | 7/8 | 7/8 | 3.6 + (2–4) |
| Neomycin[d] | 3/4 | 3/4 | 3.3 + (3–4) |
| U73122[e] | 8/12 | 8/12 | 0.6 + (0–2) |

[a]The number of mice with macroscopic tumors in the peritoneal cavity over the number of mice challenged. [b]Invasiveness was scored microscopically on a scale of 0 (non-invasive) to 4 (tumor obliterating the diaphragm); the number is the average invasiveness of all diaphragm tumors (not including mice which did not present tumors on the diaphragm), the range of invasiveness is shown in the parentheses. [c]Control consists of two independent experiments of 4mice each. In the first experiment, mice were injected intraperitoneally with 0.1 ml 10% DMSO in HBSS (diluent) q4d; in the second experiment the treatment consisted of U73343 (12 µg/ml) in diluent. These two groups are listed together as there was no difference between them. [d]Neomycin (150 µg/ml) was injected intraperitoneally q4d in diluent. [e]U73122 treatment consisted of three groups. In the first experimental series 5 mice were injectedq4d at 12 µg/ml; 3 of these mice formed tumors. The second experimental series consisted of three groups: the U73343-treated Control mice and two U73122 treatment groups, 4 mice were treated q4d at 12 µg/ml (2 formed tumors) and 3 mice (a fourth mouse died before initiation of treatment) received 24 µg/ml (3 formed tumors).

Up-regulated epidermal growth factor receptor signaling has been correlated with tumor invasion and metastasis (21, 78–81). However, the cell properties responsible for this increased progression are unknown. The present invention demonstrates that in vivo invasiveness of DU-145 cells depends on epidermal growth factor receptor signaling via phospholipase C and is independent of epidermal growth factor receptor-mediated cell proliferation.

Epidermal growth factor receptor-mediated cell motility may, in part, promote tumor cell invasiveness (80, 82). A panel of DU-145 cells were utilized which have been genetically-engineered to overexpress either WT epidermal growth factor receptor, which promote both cell motility and proliferation, or c'973 epidermal growth factor receptor, which are fully mitogenic but non-motogenic (36). The WT DU-145 cells invaded a human extracellular matrix in vitro to a greater extent than Parental DU-145 cells. Expression of c'973 epidermal growth factor receptor negatively regulated DU-145 invasiveness by downregulating endogenous WT epidermal growth factor receptor (82). When inoculated either into the prostate or the peritoneal cavity of athymic mice, the same pattern was observed, i.e., WT DU-145 cells were the most invasive, whereas c'973 DU-145 were virtually non-invasiveness.

These results may have been secondary to altered cell growth rates, but in vitro all three sublines proliferated at indistinguishable rates. While it is difficult to assess cell growth in vivo; programmed cell death was not responsible for the lesser invasiveness of Parental and, especially, c'973 DU-145 cells as few (<5%) apoptotic cells were detected in any of the tumors examined. It is possible that the smaller size and number of the c'973 DU-145 tumors in the peritoneal cavity was due to decreased growth secondary to a failure of the cells to spread within the cavity or adhere to underlying structures. Failure to induce neovascularization also may have limited the size of c'973 DU-145 tumors, as autocrine binding of ligand by the non-down-regulating c'973 epidermal growth factor receptor may prevent angiogenic transforming growth factor-α from spreading beyond the tumor mass. However, these factors can not explain the markedly fewer tumors noted.

More plausibly, the increased invasiveness of the WT DU-145 tumors was secondary to other epidermal growth factor receptor-mediated effects. Epidermal growth factor receptor-mediated proliferation is separable from motility (36, 87). WT epidermal growth factor receptor signals both mitogenesis and motility, but c'973 epidermal growth factor receptor induces only mitogenesis while down-regulating endogenous WT epidermal growth factor receptor (82, 36). Thus, cell motility may contribute to invasiveness by specifically disrupting the motogenic pathway. U73122, a pharmacologic agent which inhibits PLC (88, 89), inhibits epidermal growth factor receptor-mediated cell motility but not mitogenesis (37). U73122 had no effect on DU-145 cell proliferation in vitro. When athymic mice were inoculated intraperitoneally with wild type DU-145 cells, equal number and size of tumors were formed in the presence or absence of U73122. However, the tumors were significantly less invasive after treatment with U73122, being less invasive than Parental DU-145 and similar in invasiveness to cells expressing the non-motogenic c'973 epidermal growth factor receptor. Thus, invasiveness is a tumor property which can be modulated or inhibited independently of tumor growth.

These data strongly support a major role for cell motility as the epidermal growth factor receptor-mediated behavior linked to tumor progression. Other mechanisms may also required for tumor invasiveness. Many reports attest to the necessity of proteases in the invasive process. All three DU-145 sublines produce copious amounts of collagenases, UPa, and other proteases (82), even though c'973 DU-145 tumors were essentially non-invasive. This suggests that, while proteolysis is required for invasiveness, other properties, such as motility may play a major regulatory role in tumor invasiveness. The demonstrates the feasibility of targeting cell motility mechanisms as novel targets for control of nascent and metastasized tumors.

The present invention has demonstrated that inhibition of phospholipase C signaling reduced prostate cancer invasion and metastasis of human prostate cells. Inhibition of tumor invasiveness may be secondary to a mechanism other than diminished growth factor-induced cell motility, either affecting a different downstream pathway or a PLC isoform other than PLCγ-1.

To precisely define the critical role of the growth factor receptor-PLCγ signaling pathway, targeted molecular intervention was used. A dominant-negative PLCγ fragment, PLCz (2), includes the SH2, SH3 and phospholipase inhibitory domains and specifically inhibits activation of PLCγ and not other isoforms. Expressed in fibroblasts and glioblastoma tumor cells PLCz prevents induced cell motility and invasiveness. A cDNA encoding this fragment was stably introduced into DU-145 prostate tumor cells being driven, either by a constitutive promoter (SV40 early promoter) or a steroid hormone-responsive promoter (MMTV LTR). Expression of this dominant-negative PLC fragment resulted in greatly diminished tumor invasiveness and spread.

EXAMPLE 23

Animals

Male athymic BALB/c nu/nu mice were from the Animal Production Area of the National Cancer Institute-Frederick Cancer Research and Development Center (Frederick, Md.). The mice were housed in laminar flow cabinets under specific-pathogen-free conditions and used at 6–8 weeks of age and weighed 20–27 grams.

EXAMPLE 24

Cell Culture and Establishment of Infectant Cell Lines

WT DU-145 prostate carcinoma cells were generated as described above. These cells express levels of EGFR that do not undergo autocrine ligand-induced downregulation as they are in excess to the degradation trafficking pathway. The cells were maintained in high glucose (4.5 gm/L) Dulbecco's modified Eagle's medium (DMEM) (Gibco, NY) media supplemented with fetal bovine serum (FBS; 7.5%), penicillin (100 U/ml), streptomycin (200 µg/ml), non-essential amino acids, sodium pyruvate (1 mM) and glutamine (2 mM) (37° C., 90% humidity, 5% $CO_2$) and G418 (1000 µg/ml). All cells were cultured in the absence of G418 for at least 3 days prior to testing. Cells were passaged at subconfluence by trypsinization (0.25%, 1 mM EDTA).

PLCz was expressed in the WT DU-145 cells by lipid-mediated transfection. Briefly, PLCz was cloned into the pXf vector for constitutive expression from the SV40 early promoter or the pDexMTX vector for steroid hormone inducible expression from the MMTV LTR. In addition, a control pXf construct expressed short peptides to account for transfection and selection procedures. These were introduced into the WT DU-145 cells with the lipfectin reagent. Stable transfectant cells were selected in the above media supplemented with methotrexate (1.2 µg/ml). The expression of PLCz was determined by immunoblotting of whole cell lysates using antibodies which recognize the Z region of PLCγ-1 (Transduction Laboratories and Santa Cruz Biologicals).

EXAMPLE 25

Tumor Cell Inoculations

This investigation utilized the intraperitoneal mouse xenograft model for invasiveness as determined by diaphragmatic invasion. Tumor cells ($2 \times 10^6$) for intraperitoneal injections were suspended in HBSS (total volume, 200 µl) and injected (26.5-gauge needle, 1 ml disposable syringe) intot he peritoneal cavity. Mice were killed by $CO_2$-induced hypoxia at 45 days post-inoculation. All lobes of the mouse prostate (anterior, ventral and dorsal/lateral), regional lymph nodes (preaortic or axillary), kidneys, spleen, pancreas, liver, lungs and diaphragm were fixed in 10% buffered formalin, paraffin embedded, serially sectioned, and stained with hematoxylin and eosin.

EXAMPLE 26

Expression of PLCz Diminshes WT DU-145 Tumor Invasiveness and Spread

Mice (5 per group) were inoculated with WT DU-145 cells containing the various PLCz constructs. In the first experimental series, prostate tumor cells expressing the dominant-negative PLCz fragment from either transcription promoter, pXf or pDexMTX, were compared to non-transfected WT DU-145 cells (TABLE 3). The untransfected cells grew aggressively with 3 of the 5 mice dying early. The tumors in the mice sacrificed on day 45 were highly invasive and spread throughout the peritoneal cavity. The transfectant lines exhibited much less invasiveness and spread to a lesser degree throughout the peritoneal cavity. In the second series, growth and invasiveness of these transfectant cells were compared to the two different control constructs. Again, the control construct transfectant cells formed agressive and invasive tumors, killing two of the mice early. The PLCz-expressing tumor cells were less spread and significantly less invasive.

TABLE 3

PLCz expression and WT DU-145 prostate tumor invasiveness

| Treatment | Tumor formation[a] | Diaphragm tumors | Diaphragm Invasiveness[b] |
|---|---|---|---|
| no construct | 5/5 | 2/2[c] | 3.5 + (3–4) |
| pXf vector controls | 10/10 | 8/8[d] | 2.8 + (0–4) |
| pXf/PLCz | 9/10 | 9/10 | 1.0 + (0–2) |
| pDexMTX/PLCz | 7/10 | 6/10 | 0.5 + (0–1) |

[a]The number of mice with macroscopic tumors in the peritoneal cavity over the number of mice challenged. [b]Invasiveness was scored microscopically on a scale of 0 (non-invasive) to 4 (tumor obliterating the diaphragm); the number is the average invasiveness of all diaphragm tumors (not including mice which did not present tumors on the diaphragm), the range of invasiveness is shown in the parentheses. [c]Three mice died with extensive tumors and could notbe necropsied to ascertain diaphragm invasiveness. [d]Two mice died with extensive tumors and could not be necropsied to ascertain diaphragm invasiveness.

EXAMPLE 27

PLCz is Expressed in the Tumors from Both the SV40 Early Promoter and the MMTV LTR.

The transfectant WT DU-145 tumors that contained cDNA encoding PLCz were significantly less invasive and spread than the untransfected or control transfectant lines. PLCz protein should be detectable in these tumors, if this is related to abrogation of PLCγ signalling. PLCz protein was detectable in vitro only in the pXf/PLCz transfectant lines; a similarly sized ~51 kDa fragment was not noted. This was expected as the media did not contain steroid hormones to induce expression from the MMTV LTR in the pDexMTX/PLCz transfectant.

Figure 12A:
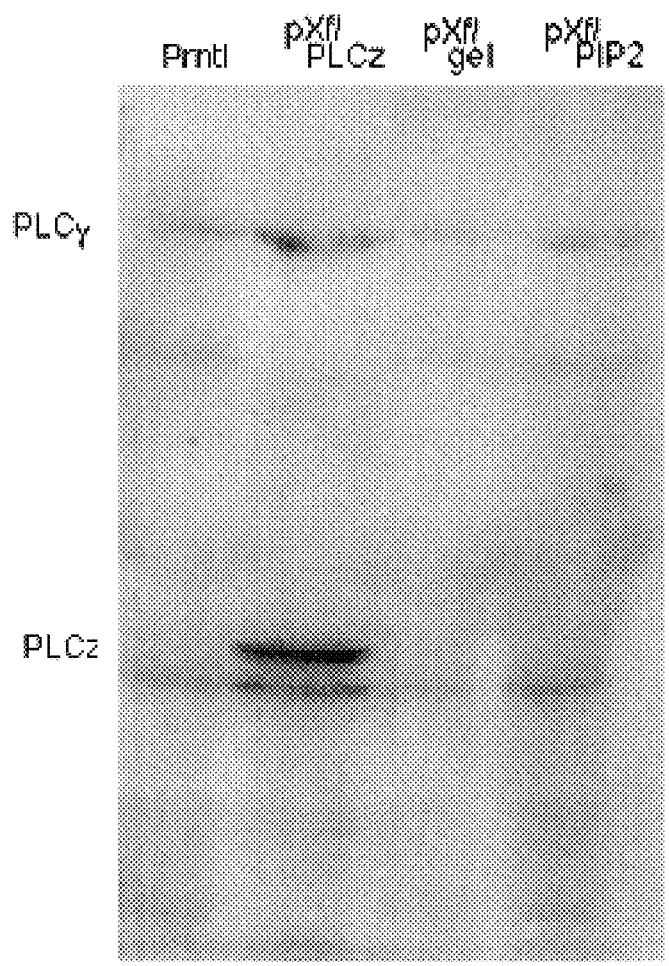
FIG. 12 shows the expression of PLCz fragment in transfectant WT DU-145 cells (left panel) and derived tumors (right panel). Protein lysates were made from these cells or tumors, and analyzed by immunoblotting using either a mixed monoclonal antibody preparation (cells, left panel) or polyclonal antisera (tumors, right panel). Both of these antibody preparations recognize epitopes in the Z-region of PLCγ-1. The endogenous PLCγ and the PLCz fragments are demarcated.
Figure 12B:
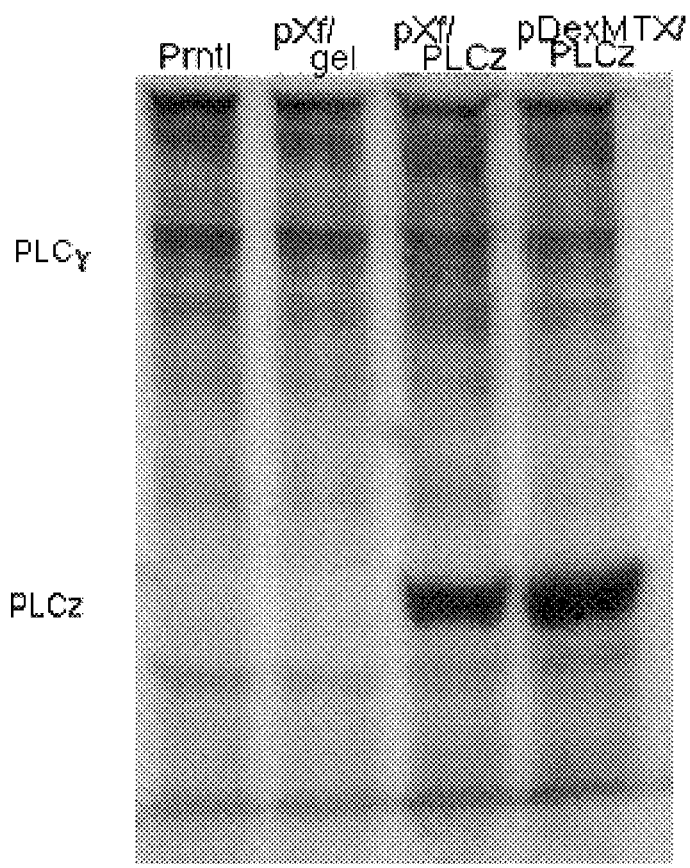

In vivo endogenous steroid hormones can activate transcription from the MMTV LTR. Tumors were isolated from the diaphragm surface of the inoculated mice and protein extracts analyzed by SDS-PAGE followed by immunoblotting for PLCγ. As noted in the right panel of FIG. 12, PLCz could be detected at levels comparable to or higher than endogenous PLCγ in tumors derived from both pXf/PLCz and pDexMTX/PLCz transfectant DU-145 prostate cells.

The present invention demonstrates a requirement for PLCγ signaling in prostate tumor invasiveness and subsequent metastasis. However, even using a rather specific pharmacologic inhibitor of PLC activity, U73122, one could not demonstrate that the EGPR-PLCγ signalling pathway was the critical element. Molecular genetic disruption of PLCγ activation and signalling was necessary to identify PLCγ as the target and not other PLC isoforms or pathways. The present invention also demonstrated that disruption of signalling by a dominant-negative PLCγ fragment, PLCz, also resulted in greatly diminished tumor invasiveness. The concordance of the findings that both pharmacologic inhibition and molecular targeting decrease tumor invasiveness illustrates the central role of PLCγ signalling in prostate tumor invasion.

The following references were cited herein:
1. Stracke M L, et al., In vivo, 8, 49–58, 1994.
2. Price J E, Journal of Cellular Biochemistry, 56, 16–22, 1994.
3. Jarrard D F, et al., Prostate, 24, 46–53, 1994.
4. Crowley C W, et al., Proc. Natl Acad Sci. 90, 5021–5025, 1993.
5. Monsky W L, et al., Cancer Research, 53, 3159–3164, 1993.
6. Aznavoorian S, et al., Cancer, 71, 1368–1383, 1993
7. Sato H, et al. Nature, 370, 61–65, 1994.
8. Strongin A Y, et al. J. of Biol. Chem., 268, 14033–14039, 1993.
9. Ponton A, et al. Cancer Research, 51, 2138–2143, 1991.
10. Mohanam S, et al. Clin. & Exper. Metastasis, 13, 57–62, 1995.
11. Schor S L, et al. Cancer Investigation, 8, 665–667, 1990.
12. Wernert N, et al., 1994 Cancer Research, 54, 5683–5688.
13. Aaronson S A, 1991 Science, 254, 1146–1153.
14. Schlegel J, et al., 1994 Inter'l Journal of Cancer, 56, 72–77.
15. Collins V P, 1993 Seminars in Cancer Biology, 4, 27–32.
16. Neal D E, et al., 1985 Lancet, i, 366–368.
17. Nguyen P L, et al., 1994 Amer. J. of Clin. Path., 101,166–176.
18. Yasui W, et al., 1988 Cancer Research, 48, 137–141.
19. Klijn J G, et al., 1992 Endocrine Reviews, 13, 3–17.
20. Sainsbury J R C, et al., 1987 Lancet, i, 1398–1402.
21. Radinsky R, et al., 1995 Clinical Cancer Research, 13,191–195.
22. Yu D, et al., 1994 Cancer Research, 54, 3260–3266.
23. Holting T, et al., 1995 Eur. J. of Endocrinology, 132, 229–235.
24. Morris G L, et al., 1990 Journal of Urology, 143, 1272–1274.
25. Davies P, et al., 1989 The Prostate, 14, 123–132.
26. Eaton C L, et al., 1988 J. of Steroid Biochemistry, 30, 341–345.
27. Myers R B, et al., 1993 Modern Pathology, 6, 733–737.
28. Ching K Z, et al., 1993 Mol. and Cellular Bio., 126, 151–158.
29. Tillotson J K, et al., 1991 Cancer Letters, 60, 109–112.
30. Stone K, et al., 1978 International J. of Cancer, 21, 274–281.
31. Connolly J M, et al., 1992 The Prostate, 20, 151–158.
32. Yoshida K, et al., 1990 Japanese J. of Cancer Res., 81, 793–798.
33. Matrisian L M, et al., 1990 Current Topics in Developmental Biology, 24, 219–254.
34. Thorne H J, et al.1987 International J of Cancer, 40, 207–212.
35. Lichtner R B, et al., 1993 Clin.& Exper. Metastasis, 11, 113–25
36. Chen P, et al., 1994 Journal of Cell Biology, 124, 547–555.
37. Chen P, et al., 1994 Journal of Cell Biology, 127, 847–857.
38. Siegal G P, et al., 1993 Cancer Letters, 69, 123–132.
39. Wells A, et al., 1990 Science, 247, 962–964.
40. Ullrich A, et al., 1984 Nature, 307, 418–425.
41. Welsh J B, et al., 1991 Journal of Cell Biology, 114, 533–543.
42. Haigler H T, et al., 1980 J. of Biol. Chem., 255, 1239–1241.
43. Kleinman H K, et al., 1982 Biochemistry, 24, 6188–6193.
44. Vukicevic S, et al., 1992 Experimental Cell Research, 202, 1–8.
45. Sunada H, et al., 1986 Proc. Natl Acad Sci, 833825–3829.
46. Reddy C C, et al., 1994 Biotechnology Progress, 10, 377–384.
47. Heussen C, et al., 1980 Analytical Biochemistry, 102, 196–202.
48. Kuo B S, et al., 1988 Jour. of Clin. Invest., 81, 730–737.
49. Wiley H S, et al., 1991 J. of Biol. Chem, 266, 11083–11094.

50. Reddy C, et al., 1995 *Journal of Cellular Physiology*, 407–419.
51. Chen W S, et al., 1989 *Cell*, 59, 33–43.
52. Gates R E, et al., 1985 *Biochemistry*, 24, 5209–5215.
53. Wells A, et al., 1988 *Mol. and Cellular Biology*, 8, 4561–4565.
54. Felder S, et al., 1992 *Journal of Cell Biology*, 117, 203–212.
55. Walton G M, et al., 1990 *J. of Biol. Chem*, 265, 1750–1754.
56. Collier I E, et al., 1988 *J. of Biol. Chem*
57. Wilhelm S M, et al., 1989 *J. of Biol. Chem*, 264, 17213–17221.
58. McGuire P G, et al., 1989 *Journal of Cellular Bioc.*, 40, 215–227.
59. Goodly L J, et al., 1995 *Tumor Biology*, in press.
60. Stephenson R A, et al., 1992 *J. of the National Cancer Institute*, 84, 951–957.
61. Ware J L, 1993 *Cancer and Metastasis Reviews*, 12, 287–301.
62. Stetler-Stevenson W G, et al., 1989 *Journal of Biological Chemistry*, 264, 17374–17378.
63. Sreenath T, et al., 1992 *Cancer Research*, 52, 4942–4947.
64. Partin A W, et al., 1994, *Benign and malignant prostatic neoplasms: human studies*. San Diego, Calif.: Acad. Press.
65. Sandberg A A, 1992, *Cytogenetic and molecular genetic aspects of human prostate cancer: primary and metastatic*. New York: Plenum Press.
66. Geldof A A, et al., 1990, *Anticancer Res*, 10, 1303–1306.
67. Linehan W M, 1995, *J Natl Cancer Inst*, 87, 331–332.
68. Gittes R F, 1991, *N Engl J Med*, 324, 236–245.
69. Surya B V, et al., 1989, *J Urol*, 142, 921–928.
70. McKeehan W L, 1986, *Nature*, 321, 629–630.
71. Chaproniere D M, et al., 1985, *J Cell Physiol*, 122, 249–253.
72. Marti U, et al., 1989, *Hepatology*, 9, 126–138.
73. Connolly J M, et al., 1989, *Prostate*, 15, 177–186.
74. Nishi N, et al., 1988, *Prostate*, 13, 209–220.
75. Wilding G, et al., 1989, *Prostate*, 15, 1–12.
76. Liu X-H, et al., 1993, *Journal of Clinical Endocrinology and Metabolism*, 77, 1472–1478.
77. Lubrano C, et al., 1989, *J Ster Biochem*, 34, 499–504.
78. Haugen D R F, et al., 1993, *Int J Cancer*, 55, 37–43.
79. Hamada J, et al., 1995, *Cancer Letters*, 89, 161–167.
80. Chakrabarty S, et al., 1995, *Clinical and Experimental Metastasis*, 13, 191–195.
81. Korc M, et al., 1992, *J Clin Invest*, 90, 1352–1360.
82. Xie H, et al., unpublished
83. National Technical Information Service, 1981–82, *Registry of Toxic Effects of Chemical Substance*. Washington D.C.: U.S. Department of Commerce.
84. Peterson G, et al., 1993, *Prostate*, 22, 335–345.
85. Knox J D, et al., 1993, *Invasion and Metastasis*, 13, 325–331.
86. Powell W C, et al., 1993, *Cancer Res*, 53, 417–422.
87. Chen P, et al., unpublished
88. Bleasdale J E, et al., 1990, *J Pharm Exp Ther*, 255, 756–768.
89. Powis G, et al., 1992, *Cancer Res*, 52, 2835–2840.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of inhibiting progression of a carcinoma in an individual in need of such treatment, comprising the step of administering to said individual a pharmacologically effective dose of a phospholipase C inhibitor, wherein said inhibitor is selected from the group consisting of U73122 (1-(6-((17β-3-methoxyestra-1,3,5(10)-trien-17-yl)amino) hexyl)-1H-pyrrole-2,5-dione) and RHC-80267 (1,6-bis-(cyclohexyloximinocarbonylamino)-hexane).

2. The method of claim 1, wherein said phospholipase C inhibitor is administered in a dose of from about 0.1 mg/kg to about 2 mg/kg.

3. A method of inhibiting metastasis of a carcinoma in an individual in need of such treatment, comprising the step of administering to said individual a pharmacologically effective dose of a phospholipase C inhibitor, wherein said inhibitor is selected from the group consisting of U73122 (1-(6-((17β-3-methoxyestra-1,3,5(10)-trien-17-yl)amino) hexyl-1H-pyrrole-2,5-dione) and RHC-80267 (1,6-bis-(cyclohexyloximinocarbonylamino)-hexane).

4. The method of claim 3, wherein said phospolipase C inhibitor is administered in a dose of from about 0.1 mg/kg to about 2 mg/kg.

* * * * *